_(12)_ United States Patent
Yamamoto

(10) Patent No.: US 9,220,560 B2
(45) Date of Patent: Dec. 29, 2015

(54) INSTRUMENT FOR ENDOSCOPIC TREATMENT

(75) Inventor: Hironori Yamamoto, Shimotsuke (JP)

(73) Assignee: JICHI MEDICAL UNIVERSITY, Shimotsuke-Shi (JP)

( * ) Notice: Subject to any disclaimer, the term of this patent is extended or adjusted under 35 U.S.C. 154(b) by 1671 days.

(21) Appl. No.: 11/992,515

(22) PCT Filed: Sep. 12, 2006

(86) PCT No.: PCT/JP2006/318032
§ 371 (c)(1),
(2), (4) Date: Mar. 25, 2008

(87) PCT Pub. No.: WO2007/034708
PCT Pub. Date: Mar. 29, 2007

(65) Prior Publication Data
US 2009/0247823 A1    Oct. 1, 2009

(30) Foreign Application Priority Data
Sep. 26, 2005    (JP) .................................. 2005-278473

(51) Int. Cl.
*A61B 18/14*    (2006.01)
*A61B 17/32*    (2006.01)
(Continued)

(52) U.S. Cl.
CPC ........... *A61B 18/1492* (2013.01); *A61B 18/149* (2013.01); *A61B 17/320068* (2013.01); *A61B 18/1445* (2013.01); *A61B 2017/00269* (2013.01);
(Continued)

(58) Field of Classification Search
CPC ............. A61B 2018/00601; A61B 2018/1405; A61B 2018/1465; A61B 2018/1467; A61B 2018/00488; A61B 2018/00494; A61B 18/005; A61B 2018/0016; A61B 2018/142; A61B 17/320068; A61B 18/1445; A61B 18/149; A61B 18/1492; A61B 2017/00269; A61B 2018/00482; A61B 2018/126; A61B 2018/1422; A61B 2019/481
USPC ................................................ 606/46, 50, 49
See application file for complete search history.

(56) References Cited

U.S. PATENT DOCUMENTS 5,549,605 A * 8/1996 Hahnen ........................... 606/46
5,766,215 A    6/1998 Muri et al.
(Continued)

FOREIGN PATENT DOCUMENTS

FR    2 662 084 A1    11/1991
JP    8-299355 A    11/1996
(Continued)

OTHER PUBLICATIONS

Extended European Search Report, dated Feb. 6, 2013, issued in EP Patent Application No. 06797839.5.
(Continued)

*Primary Examiner* — Jaymi Della
(74) *Attorney, Agent, or Firm* — Birch, Stewart, Kolasch & Birch, LLP

(57) ABSTRACT

A treatment instrument for an endoscope is provided that is suitable for cutting submucosa in endoscopic submucosal dissection. The treatment instrument for an endoscope includes a treatment portion having a cutting unit at a tip of an insertion portion that is to be inserted into the body. The main unit of the treatment portion is formed in a sawtooth shape having a peak portion and a valley portion. An electrode plate serving as the cutting unit is provided in the valley portion.

23 Claims, 24 Drawing Sheets

(51) Int. Cl.
  *A61B 17/00* (2006.01)
  *A61B 18/00* (2006.01)
  *A61B 19/00* (2006.01)
  *A61B 18/12* (2006.01)

(52) U.S. Cl.
  CPC ............... *A61B 2018/00482* (2013.01); *A61B 2018/00601* (2013.01); *A61B 2018/126* (2013.01); *A61B 2018/1422* (2013.01); *A61B 2018/1467* (2013.01); *A61B 2019/481* (2013.01)

(56) References Cited

U.S. PATENT DOCUMENTS

| | | | |
|---|---|---|---|
| 5,925,040 A * | 7/1999 | Nardella et al. | 606/41 |
| 6,015,406 A | 1/2000 | Goble et al. | |
| 6,135,999 A | 10/2000 | Fanton et al. | |
| 6,142,993 A * | 11/2000 | Whayne et al. | 606/41 |
| 6,251,108 B1 | 6/2001 | Irion et al. | |
| 6,273,887 B1 | 8/2001 | Yamauchi et al. | |
| 6,805,128 B1 | 10/2004 | Pless et al. | |
| 7,494,488 B2 | 2/2009 | Weber | |
| 2001/0025190 A1 * | 9/2001 | Weber et al. | 607/89 |
| 2001/0041893 A1 | 11/2001 | Bartel | |
| 2003/0130654 A1 | 7/2003 | Kasahara et al. | |
| 2003/0212396 A1 | 11/2003 | Eggers et al. | |
| 2004/0167514 A1 | 8/2004 | Okada | |
| 2004/0210215 A1 * | 10/2004 | Okada | 606/45 |
| 2004/0225287 A1 | 11/2004 | Suzuki | |
| 2005/0055073 A1 | 3/2005 | Weber | |

FOREIGN PATENT DOCUMENTS

| | | |
|---|---|---|
| JP | 9-262239 A | 10/1997 |
| JP | 2000-506405 A | 5/2000 |
| JP | 2002-95671 A | 4/2002 |
| JP | 2003-199765 A | 7/2003 |
| JP | 2004-275641 A | 10/2004 |
| JP | 2004-321660 A | 11/2004 |
| WO | WO 90/07303 A1 | 7/1990 |
| WO | WO 97/07747 A1 | 3/1997 |

OTHER PUBLICATIONS

Extended European Search Report, dated Feb. 6, 2013, issued in EP Patent Application No. 12197488.5.

Extended European Search Report, dated Feb. 6, 2013, issued in EP Patent Application No. 12197490.1.

KR Office Action issued in corresponding KR Application No. 10-2008-7007289 on Nov. 16, 2012.

* cited by examiner

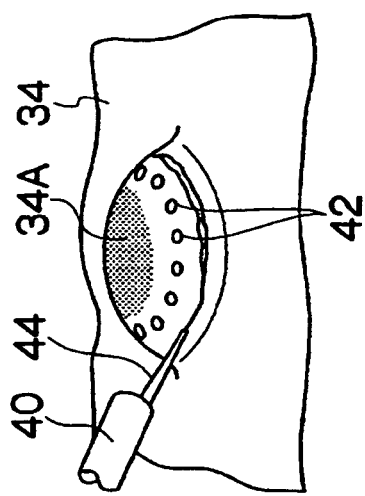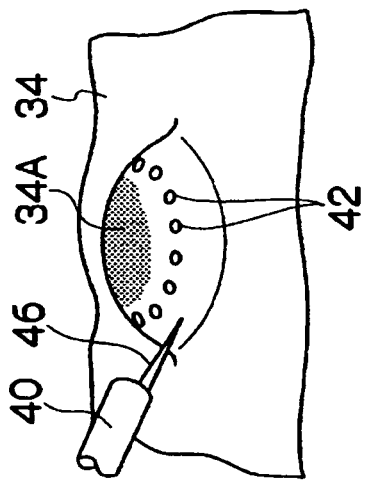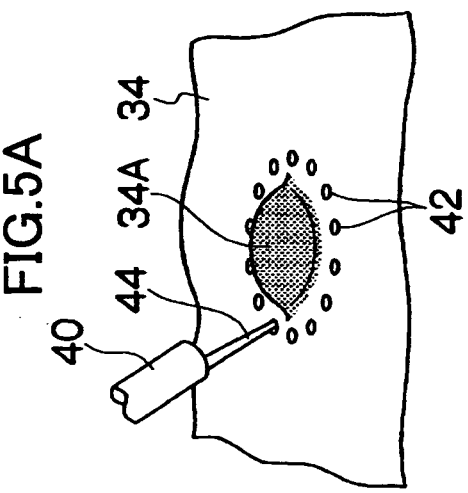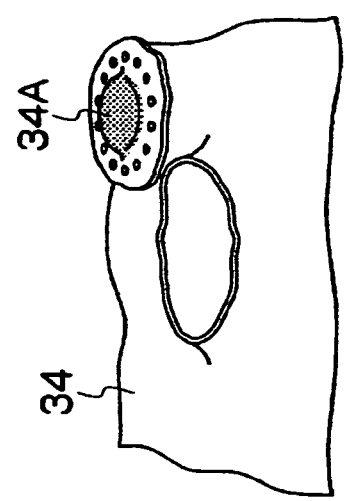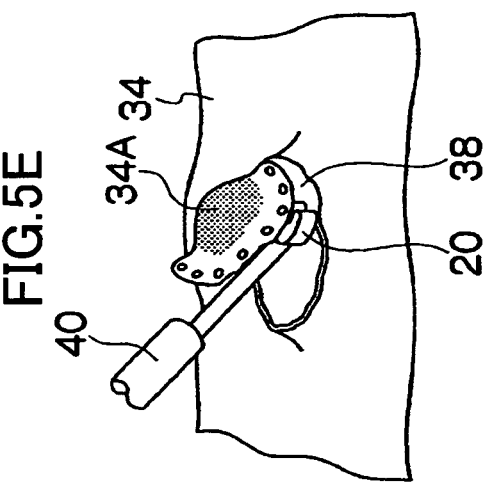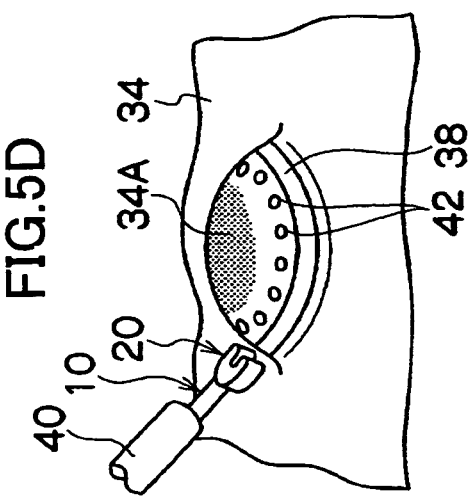

INSTRUMENT FOR ENDOSCOPIC TREATMENT

CROSS-REFERENCE TO RELATED APPLICATIONS

This application is a National Stage Entry under 35 U.S.C. §371 of PCT/JP2006/318032 filed on Sep. 12, 2006, which claims priority of Japanese Patent Application No. 2005-278473 filed in Japan on Sep. 26, 2005, the entire contents of which are hereby incorporated by reference.

BACKGROUND OF THE INVENTION

1. Technical Field

The present invention relates to a treatment instrument for an endoscope, and more particularly to a treatment instrument for an endoscope that is used for endoscopic submucosal dissection (ESD).

2. Background Art

Endoscopic mucosal resection is recognized as a minimally invasive and reliable treatment that is useful as a radical operation for neoplastic mucosal lesions such as early gastric cancer and early colorectal cancer. In recent years, a method referred to as endoscopic submucosal dissection (ESD) has been developed and brought into widespread use as a method that applies endoscopic mucosal resection to enable reliable en bloc resection of a lesion that extends over a wider area. In this method, en bloc resection of neoplastic mucosa is performed by dissecting submucosa between the mucosa and muscularis propria, after dissection of peritumoral mucosa. With this method, while it is possible to make a dissection line in the manner intended and to reliably resect a tumor, on the other hand there have been the problems that the method involves a high level of technical difficulty, the treatment requires skill and experience, and the treatment time is long.

Various treatment instruments for endoscopes have been proposed to solve these problems. For example, a treatment instrument for an endoscope disclosed in Patent Document 1 is a hook knife in which a high-frequency electrode at the tip is formed with a curved rod. By hooking the tip of the hook knife in mucosa tissue and drawing it into a sheath, the mucosa tissue is dissected. Further, a treatment instrument for an endoscope disclosed in Patent Document 2 is an IT knife in which an insulator is attached to the tip of an acicular surgical knife so that piercing of muscularis propria is prevented by the insulator. By using these treatment instruments for endoscopes, it is attempted to overcome even to a small degree some of the technical difficulty in performing endoscopic submucosal dissection.

Patent Document 1: Japanese Patent Application Laid-Open No. 2004-275641
Patent Document 2: Japanese Patent Application Laid-Open No. 8-299355

SUMMARY AND DISCLOSURE OF THE INVENTION

Problems to be Solved by the Invention

However, the treatment instrument for an endoscope disclosed in Patent Document 1 has the problem that there is a risk that muscularis propria will be damaged depending on the angle or posture of the tip portion, and the operation thereof is difficult. Further, the treatment instrument for an endoscope disclosed in Patent Document 2 has the problem that since treatment is performed outside the range of observation images of the endoscope, operation thereof required skill and experience. Thus, with the conventional treatment instruments for endoscopes, there are the problems that the operation is difficult when performing endoscopic submucosal dissection, and it is difficult to quickly and safely perform treatment. In particular, with the conventional treatment instruments for endoscopes there is a problem that it is difficult to quickly and safely ablate (dissect) submucosa.

The present invention was made in consideration of these circumstances, and an object of this invention is to provide a treatment instrument for an endoscope which is suitable for endoscopic submucosal dissection.

Means for Solving the Problems

To achieve the foregoing object, according to a first aspect of the present invention there is provided a treatment instrument for an endoscope comprising a treatment portion having a cutting unit at a tip of an insertion portion to be inserted inside a body, characterized in that the treatment portion is provided with a peak portion and a valley portion on a distal end side and a proximal end side of, and the cutting unit is provided in the valley portion.

To achieve the foregoing object, according to a second aspect of the present invention there is provided a treatment instrument for an endoscope comprising a treatment portion having a cutting unit at a tip of an insertion portion to be inserted inside a body, characterized in that the treatment portion comprises a plurality of plate-shaped members disposed in a radial shape, on a distal end side and a proximal end side of the plate-shaped members, an outer peripheral portion is protruded to form a peak portion and thereby form a valley portion at a center section, and the cutting unit is provided in the valley portion.

To achieve the foregoing object, according to a third aspect of the present invention there is provided a treatment instrument for an endoscope comprising a treatment portion having a cutting unit at a tip of an insertion portion to be inserted inside a body, characterized in that the treatment portion is formed in a toothed-wheel shape which alternately has a peak portion and a valley portion, and the cutting unit is provided in the valley portion.

The inventors of the present invention focused on the fact that there is a large difference between the physical properties of submucosa, and those of mucosa and muscularis propria, and made use of the fact that the submucosa that is the cutting target is a mesh-like fiber that is soft and flexible to make it possible to cut only submucosa. That is, according to the first, second, and third aspects of the present invention, a treatment portion is provided with a peak portion and a valley portion, and since a cutting unit is provided in the valley portion, when the treatment portion is pushed into the submucosa, the peak portion enters into the submucosal fibers and the submucosal fibers are collected in the valley portion so that the submucosa is cut by the cutting unit. With a treatment instrument for an endoscope that is configured in this manner, when the treatment portion is pushed into muscularis propria or mucosa, since the cutting unit in the valley portion does not come in contact with the muscularis propria or mucosa even if the peak portion does come in contact therewith, there is no risk of damaging the muscularis propria or mucosa. Hence, it is possible to quickly and safely cut only the submucosa which is the cutting target. Further, according to the first and seconds aspects, since the cutting unit is disposed on the proximal end side, fibrous submucosa can be collected in the valley portion and cut by performing a pulling operation to move the treatment portion to the proximal end side.

A fourth aspect of the present invention is in accordance with the first to third aspects, characterized in that the cutting unit is an electric conductor which is connected to a high-frequency current supply unit. According to the fourth aspect, the submucosa can be cut by applying a high frequency current to an electric conductor as the cutting unit, and similarly to a case of an electrocautery device or the like, cutting can be performed without strongly affecting each tissue of the human body. In this connection, a high frequency treatment instrument may be a monopolar type in which an electric conductor forms one of a pair of electrodes, or a bipolar type in which an electric conductor forms both of a pair of electrodes. The structure of a monopolar-type high frequency treatment instrument is simple and thus a low-cost treatment instrument can be provided. In the case of a bipolar-type high frequency treatment instrument, a counter-electrode plate that is mounted on the subject is not required, and thus a treatment instrument with high safety characteristics can be provided.

A fifth aspect of the present invention is in accordance with the first to third aspects, characterized in that the cutting unit irradiates a laser beam to perform cutting. According to the fifth aspect, by irradiation of a laser beam it is possible to safely cut the submucosa.

A sixth aspect of the present invention is in accordance with the first to third aspects, characterized in that the cutting unit oscillates ultrasonic waves to perform cutting. According to the sixth aspect, by oscillation of ultrasonic waves it is possible to safely cut the submucosa.

A seventh aspect of the present invention is in accordance with any one of the first to sixth aspects, characterized in that the treatment portion is inserted through a forceps channel of an endoscope. According to the seventh aspect, the treatment instrument for an endoscope can be inserted into and withdrawn from a forceps channel of an endoscope. Hence, it is possible to switch the treatment instrument for an endoscope with another treatment instrument, and thus treatment such as endoscopic submucosal dissection can be easily performed.

An eight aspect of the present invention is in accordance with any one of the first to seventh aspects, characterized in that, in the treatment portion, a space between the peak portions can expand and contract. According to the eighth aspect, by expanding a space between peak portions to widen a valley portion, it is possible to broaden the area that can be subjected to a cutting process in one operation and thereby swiftly carry out the treatment. Further, the treatment portion can be made smaller by decreasing the space between the peak portions and thus, for example, the treatment portion can be inserted through the forceps channel of an endoscope.

A ninth aspect of the present invention is in accordance with any one of the first to eighth aspects, characterized in that the treatment portion is supported via a swivel mechanism which regulates the posture of the treatment portion. According to the ninth aspect, since the treatment portion is supported via a swivel mechanism, the posture of the treatment portion can be freely adjusted and treatment can be easily carried out.

A tenth aspect of the present invention is in accordance with any one of the first to ninth aspects, characterized in that a plurality of cutting units are provided in the valley portion, and a selection unit which selects a cutting unit to be used from among the plurality of cutting units is provided. According to the tenth aspect, since a plurality of cutting units are provided in the treatment portion and a cutting unit to be used can be selected, for example, a cutting depth can be adjusted.

An eleventh aspect of the present invention is in accordance with any one of the first to tenth aspects, characterized in that the cutting unit is disposed at a position that is separate from an end face in the thickness direction of the treatment portion. According to the eleventh aspect, since the cutting unit is disposed at a position that is separate from an end face in the thickness direction, there is no risk of cutting the muscularis propria or mucosa even when the end face in the thickness direction contacts against the muscularis propria or mucosa.

A twelfth aspect of the present invention is in accordance with any one of the first to eleventh aspects, characterized in that the peak portion is formed in a tapered shape that becomes narrower towards a distal end side thereof, and a tip thereof is rounded and has a non-incisional property. Therefore, according to the twelfth aspect of the present invention, it is easy to insert the peak portion into fibrous submucosa and cutting of the muscularis propria by the peak portion can be prevented. In this connection, the term "non-incisional property" refers to the fact that the tip does not cut any tissue by only pushing against it.

Advantage of the Invention

According to the present invention, a treatment portion is configured with a peak portion and a valley portion, and since a cutting unit is provided only in the valley portion it is possible to cut only fibrous submucosa and thus endoscopic submucosal dissection can be carried out quickly and safely.

BRIEF DESCRIPTION OF THE DRAWINGS

FIG. 5 comprises explanatory views that illustrate a method of operating the treatment instrument for an endoscope, in which FIG. 5A shows a state in which marking is being performed around a lesion, FIG. 5B shows a state in which the lesion is being made to protrude, FIG. 5C shows a state in which incision of mucosa is being performed, FIG. 5D shows a state after incision of the mucosa, FIG. 5E shows a state in which cutting of submucosa is being performed, and Figure SF shows a state after cutting of the submucosa;

FIG. 22 comprises explanatory views that describe a treatment portion having a different configuration to that shown in FIG. 3, in which

FIG. 23 comprises views that illustrate a treatment portion having a peak portion of a shape that is different to the treatment portion shown in FIG. 3 and FIG. 4, in which

FIG. 24 comprises views that illustrate a treatment portion having a peak portion of a shape that is different to the treatment portion shown in FIG. 16 and FIG. 17, in which

DESCRIPTION OF SYMBOLS

10 . . . treatment instrument for an endoscope, 12 . . . insertion portion, 14 . . . hand-side operation portion, 16 . . . flexible sheath, 18 . . . wire, 20 . . . treatment portion, 30 . . . main unit, 30A . . . peak portion, 30B . . . valley portion, 30D . . . peak portion, 30E . . . valley portion, 32 . . . electrode plate, 33 . . . electrode plate, 80 . . . treatment instrument for an endoscope, 82 . . . treatment portion, 84 . . . main unit, 84A . . . peak portion, 84B . . . valley portion, 86B . . . electrode portion, 130 . . . treatment portion, 132 . . . main unit, 132A . . . peak portion, 132B . . . valley portion, 132C . . . peak portion, 132D . . . valley portion, 134 . . . electrode plate, 136 . . . electrode plate, 140 . . . treatment portion, 142 . . . main unit, 142A . . . peak portion, 142B . . . valley portion, 142C . . . peak portion, 142D . . . valley portion, 144 . . . electrode plate, 146 . . . electrode plate, 150 . . . treatment portion, 152 . . . main unit, 152A . . . peak portion, 152B . . . valley portion, 152C . . . peak portion, 152D . . . valley portion, 154 . . . electrode element, 156 . . . electrode element DETAILED DESCRIPTION OF THE INVENTION AND BEST MODE FOR CARRYING OUT THE INVENTION Hereunder, preferred embodiments of the treatment instrument for an endoscope relating to the present invention are described in detail in accordance with the attached drawings.

Figure 1:
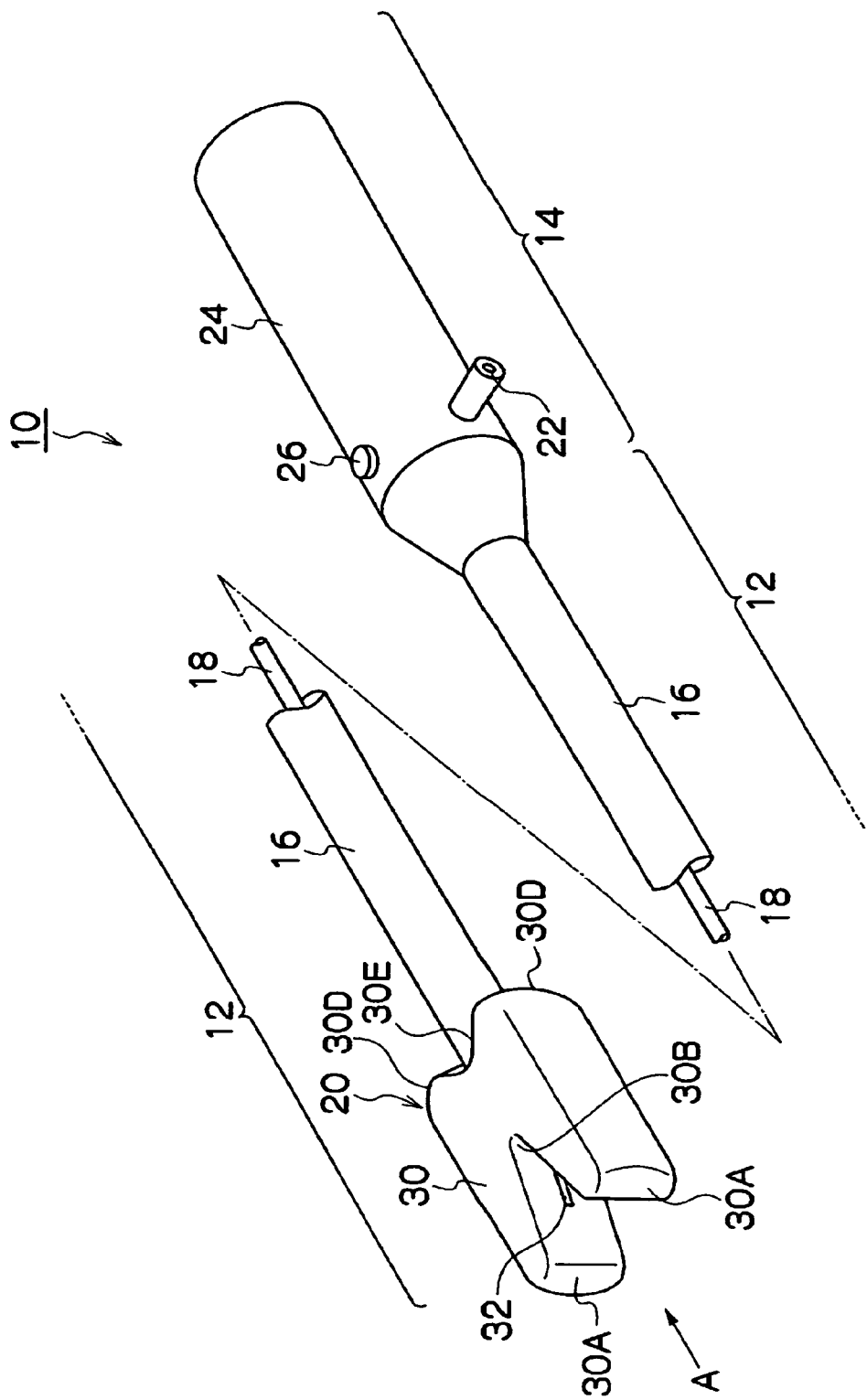
FIG. 1 is an oblique perspective view that illustrates a first embodiment of a treatment instrument for an endoscope relating to the present invention.

FIG. 1 is an oblique perspective view illustrating a treatment instrument for an endoscope 10 according to the first embodiment. As shown in the figure, the treatment instrument for an endoscope 10 chiefly comprises an insertion portion 12 that is inserted into a body cavity, and a hand-side operation portion 14 that is provided in a condition in which it is connected with the insertion portion 12. The insertion portion 12 is configured with a non-conductive flexible sheath 16, an electrically conductive wire 18 that is passed through the inside of the flexible sheath 16, and a treatment portion 20 that is attached to the tip of the flexible sheath 16. The tip of the wire 18 is connected to the treatment portion 20, and the proximal end of the wire 18 is connected to a connector 22 of the hand-side operation portion 14. A high-frequency supply apparatus (not shown) that supplies a high frequency current is electrically connected to the connector 22. An operation button 26 is provided on a grasping portion 24 of the hand-side operation portion 14. When an operation is performed to push down the operation button 26, a high frequency current is passed through the wire 18. The treatment instrument for an endoscope 10 configured as described above is operated by grasping the grasping portion 24 of the hand-side operation portion 14 and inserting or withdrawing the insertion portion 12 to or from a forceps channel (not shown) of an endoscope.

Figure 2:
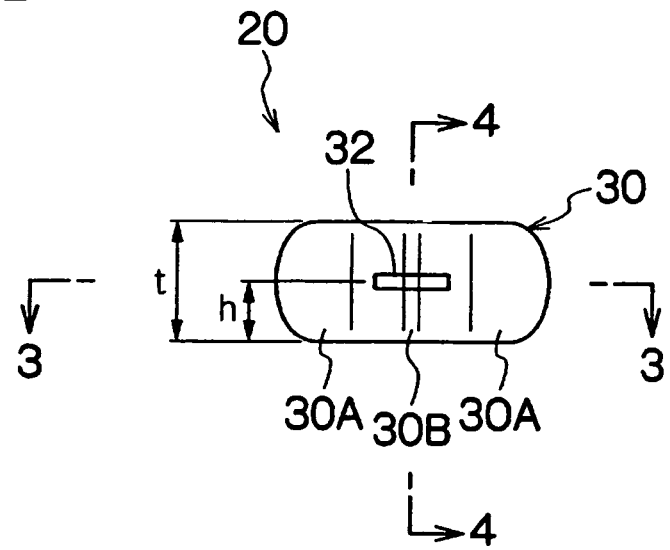
FIG. 2 is a front view of the treatment portion shown in FIG. 1.
Figure 3:
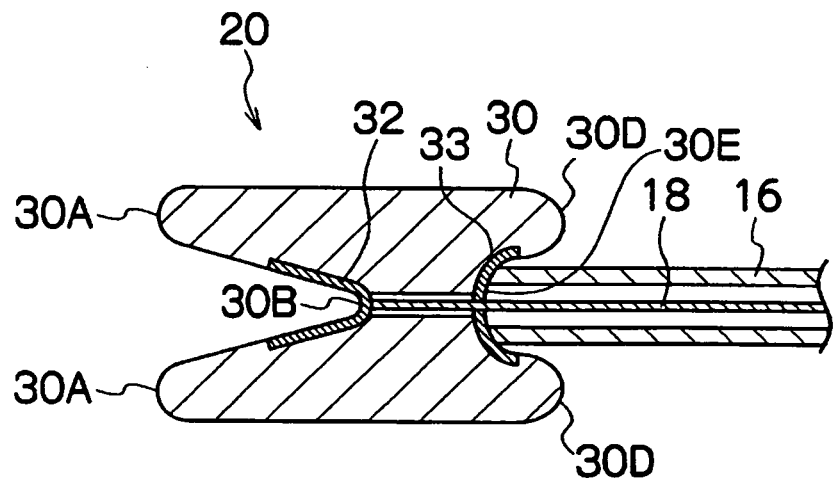
FIG. 3 is a sectional view along the line 3-3 of the treatment portion that shows a cross section in FIG. 2.
Figure 4:
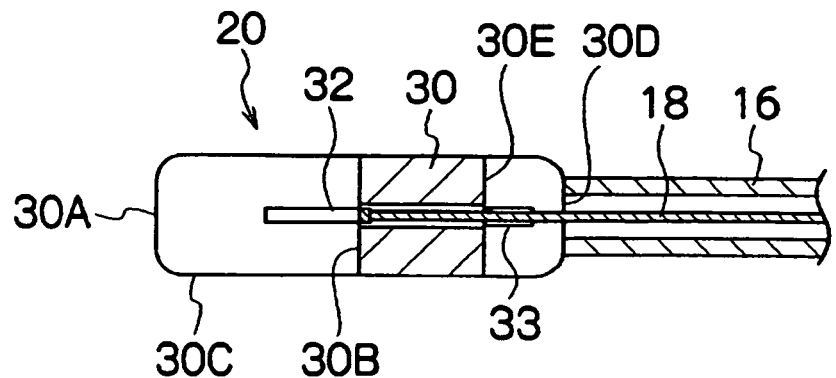
FIG. 4 is a sectional view along the line 4-4 of the treatment portion that shows a cross section in FIG. 2.

FIG. 2 is a front view of the treatment portion 20 shown in FIG. 1, as seen from the direction of the arrow A. FIG. 3 is a planar sectional view of the treatment portion 20 along a line 3-3 shown in FIG. 2. FIG. 4 is a lateral sectional view of the treatment portion 20 along a line 4-4 shown in FIG. 2.

A main unit 30 of the treatment portion 20 consists of a non-conductive material such as ceramic or plastic and is formed in a sawtooth shape having two peak portions 30A and 30A on a distal end side, a valley portion 30B disposed between the peak portions 30A and 30A, two peak portions 30D and 30D on a proximal end side, and a valley portion 30E provided between the peak portions 30D and 30D. The tips of the peak portions 30A and 30A are formed in a non-incisive obtuse shape, and is configured so that even if the peak portions 30A and 30A push against mucosa 34 or muscularis propria 36 that are described later (see FIG. 6), the peak portions 30A and 30A do not cut the tissue. More specifically, the peak portions 30A and 30A are configured to have a non-cutting property with respect to the mucosa 34 and the muscularis propria 36.

An electrode plate 32 is provided in the valley portion 30B of the main unit 30. The electrode plate 32 comprises an electric conductor such as a metal, and is electrically connected to the wire 18 as shown in FIG. 3. As described in the foregoing, the wire 18 is electrically connected to the connector 22 shown in FIG. 1, and by connecting the connector 22 to a high-frequency current supply unit (not shown), a high frequency current can be fed to the electrode plate 32. In this connection, the treatment instrument for an endoscope 10 according to the first embodiment is a monopolar type in which only one electrode is provided in the treatment portion 32, and the other electrode (counter-electrode plate) is attached to the subject.

As shown in FIG. 3, the electrode plate 32 is provided in the valley portion 30B and the tip of the electrode plate 32 is disposed at a substantially intermediate position between the top of the peak portion 30A and the bottom of the valley portion 30B. Accordingly, the configuration is such that when the peak portions 30A and 30A are contacted against the mucosa or muscularis propria, the electrode plate 32 of the valley portion 30B does not contact against the mucosa or muscularis propria. In this connection, the formation area of the electrode plate 32 is not particularly limited as long as the electrode plate 32 is not formed at the peak portion 30A. Hence, the electrode plate 32 may be formed only on the bottom portion of the valley portion 30B, or may be formed over a wide area excluding the vicinity of the top of the peak portion 30A.

As shown in FIG. 2 and FIG. 4, the electrode plate 32 is disposed at a substantially intermediate position of the main unit 30 in the thickness direction of the main unit 30. More specifically, the electrode plate 32 is disposed such that a distance h from an underside 30C of the main unit 30 is about half of a thickness t of the main unit 30. Accordingly, when the underside 30C of the main unit 30 contacts against, for example, the muscularis propria, the electrode plate 32 is separated from the muscularis propria by the distance h and thus there is no risk of the electrode plate 32 damaging the muscularis propria. The height position (i.e. the distance h) of the electrode plate 32 is not limited to half of the thickness t of the main unit 30, and the electrode plate 32 can be set at an arbitrary position from the underside 30C of the main unit 30, and a cutting position can be freely set in the height direction in accordance with the electrode plate 32.

In this connection, the peak portion 30D, the valley portion 30E, and an electrode plate 33 provided in the valley portion 30E have the same configuration as the peak portion 30A, the valley portion 30B, and the electrode plate 32, respectively, and a description of those components is omitted herein.

Next, a method of performing endoscopic submucosal dissection using the above described treatment instrument for an endoscope 10 will be described with reference to FIGS. 5A, 5B, 5C, 5D, 5E and 5F. The example hereunder describes a technique in a case in which a lesion 34A is present in mucosa 34, and the lesion 34A is removed without damaging muscularis propria 36.

First, the lesion 34A is confirmed with an observation optical system (not shown) provided in an endoscope insertion portion 40. At this time, it is good for a dye such as indigo carmine to be applied from a nozzle of the endoscope insertion portion 40 to stain the lesion 34A.

Next, as shown in FIG. 5A, markings 42, 42 . . . are made at predetermined intervals around the lesion 34A. The method of making the markings 42 is not particularly limited and, for example, a high frequency knife 44 having an acicular tip is used. The high frequency knife 44 is a device in which a thin metal conducting wire is inserted through the inside of an insulating tube and a tip of the metal conducting wire is protruded by a predetermined length from the tip of the insulating tube. The protruding portion of the metal conducting wire serves as an electrode so that a high frequency current flows to thereby dissect or resect an inner wall of the body cavity.

Next, as shown in FIG. 5B, an injection needle 46 is inserted through the forceps channel of the endoscope insertion portion 40 and led out from the tip. A drug solution is then locally injected into submucosa 38 (see FIG. 6) of the mucosa 34 around the lesion 34A by the injection needle 46. Physiological saline is generally used as the drug solution, and hyaluronate sodium that has high viscosity may also be used. By carrying out localized injection in the entire area surrounding the lesion 34A in this manner, the entire lesion 34A enters a state in which it protrudes significantly.

Subsequently, the injection needle 46 is drawn out from the forceps channel of the endoscope insertion portion 40, and the high frequency knife 44 is inserted through the forceps channel. Then, as shown in FIG. 5C, the mucosa 34 on the outer circumference of the lesion 34A is dissected with the high frequency knife 44 along the positions of the markings 42, 42 . . . . Upon completion of the dissection, as shown in FIG. 5D, the mucosa 34 of the lesion 34A contracts and the submucosa 38 can be seen.

Figure 6:
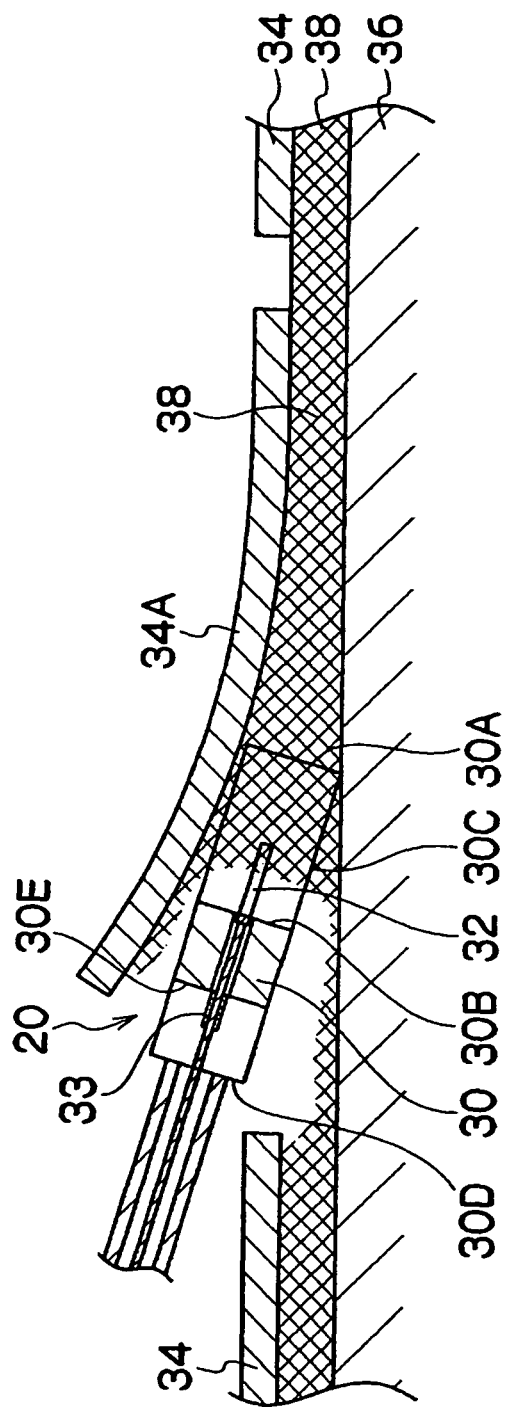
FIG. 6 is a sectional view that illustrates a cutting state.

Next, the high frequency knife 44 is drawn out from the forceps channel of the endoscope insertion portion 40, and the treatment instrument for an endoscope 10 of the present embodiment is inserted through the forceps channel to cause the treatment portion 20 to protrude out from the forceps channel. The treatment portion 20 is pressed into the submucosa 38 from the dissection position. Subsequently, as shown in FIG. 6, the treatment portion 20 is pushed against the submucosa 38 under the lesion 34A. At this time, since the peak portions 30A and 30A of the treatment portion 20 enter into the fiber of the submucosa 38, the fiber of the submucosa 38 enters between the peak portions 30A and 30A, i.e. enters the valley portion 30B. By contact of the fiber of the submucosa 38 against the electrode plate 32 as a cutting unit, a high frequency current concentrates at and flows to the submucosa 38 to perform cutting. By repeatedly performing this operation, as shown in FIG. 5E, the lesion 34A is gradually peeled off from the submucosa 38. It is thereby possible to detach the lesion 34A as shown in FIG. 5F.

At the time of the above described work to cut (dissect) the submucosa 38, even if the underside 30C of the main unit 30 contacts against the muscularis propria 36, the electrode plate 32 is separated by a distance h from the underside 30C and there is no risk that the electrode plate 32 will contact the muscularis propria 36. Hence, since there is no risk of a high frequency current concentrating at and flowing to the muscularis propria 36, damage to the muscularis propria 36 can be prevented.

Further, in a case where the peak portions 30A and 30A of the main unit 30 contact against the muscularis propria 36 or the mucosa 34 when pressing forward the treatment portion 20, since the muscularis propria 36 or mucosa 34 which are not fibers do not enter the valley portion 30B, there is no risk that the muscularis propria 36 or mucosa 34 will be cut.

Further, according to the present embodiment, cutting can also be carried out at the time of a pulling back operation to move the treatment portion 20 to the proximal end side. That is, at the time of the operation to pull back the treatment portion 20, the valley portions 30D and 30D of the main unit 30 are inserted between the fibrous submucosa 38, and since the submucosa 38 is gathered in the valley portion 32E and comes in contact with the electrode plate 33, the submucosa 38 can be safely cut. At this time, since cutting is performed while pulling back the treatment portion 20, force is easily applied to the treatment portion 20 and the submucosa 38 can be cut quickly and safely.

Thus, since the treatment instrument for an endoscope 10 only cuts submucosa 38 that is fiber, there is no risk of mistakenly cutting the muscularis propria 36 or the mucosa 34, and the submucosa 38 can be cut quickly and safely.

Figure 37:
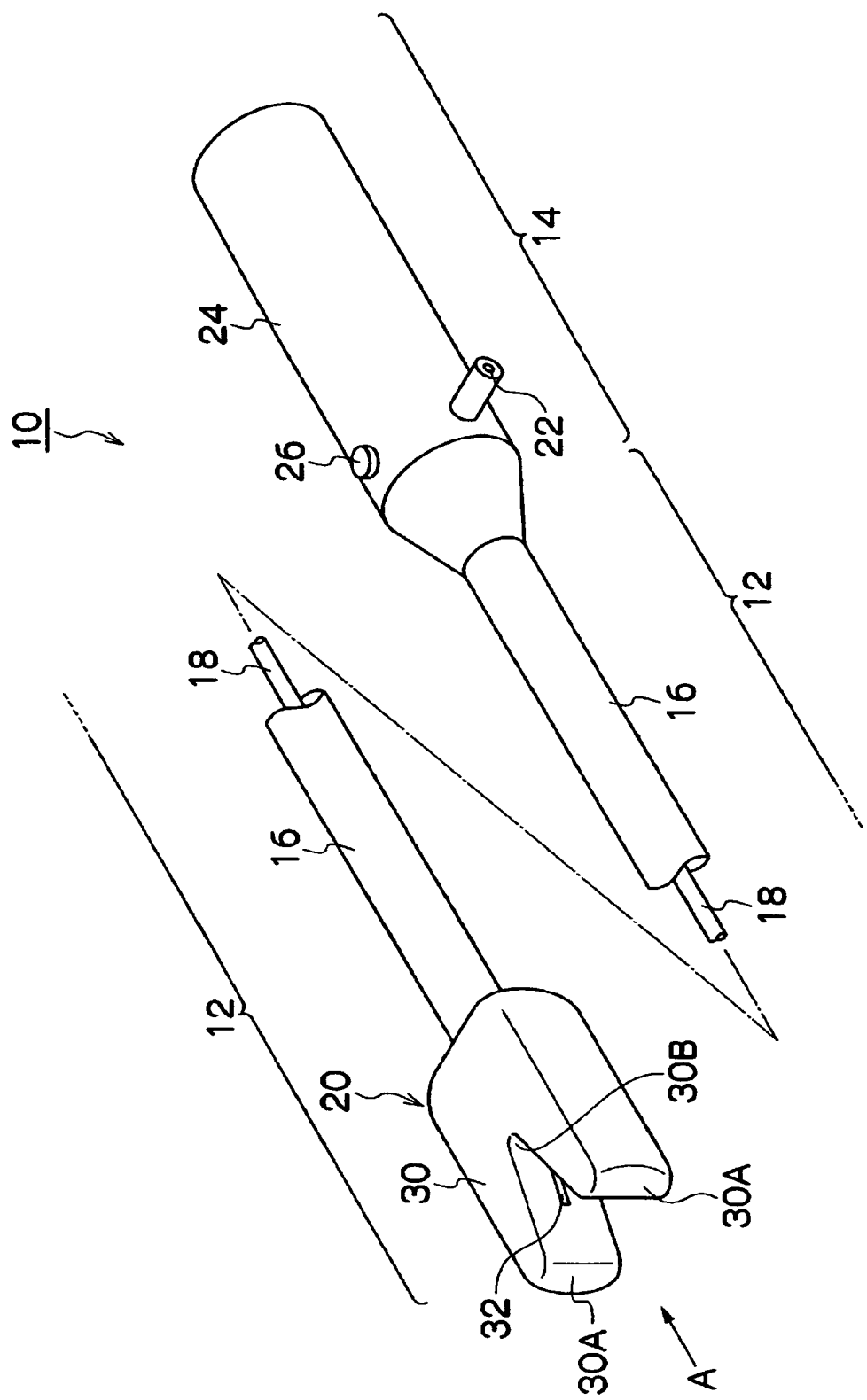
FIG. 37 is an oblique perspective view showing a state after the treatment portion shown in FIG. 1 changed shape.

In this connection, in the above-described first embodiment, peak portions 30A and 30D, valley portions 30B and 30E, and electrode plates 32 and 33 are provided at both the distal end side and the proximal end side of the treatment portion 20, however, as shown in FIG. 37, a configuration may also be adopted in which the peak portion 30A, the valley portion 30B, and the electrode plate 32 are provided only on the distal end side of the treatment portion 20. Further, although not illustrated in the drawings, a configuration may also be adopted in which the peak portion 30D, the valley portion 30E, and the electrode plate 33 are provided only on the proximal end side of the treatment portion 20. In any case, cutting of the submucosa 38 can be safely performed.

Figure 7:
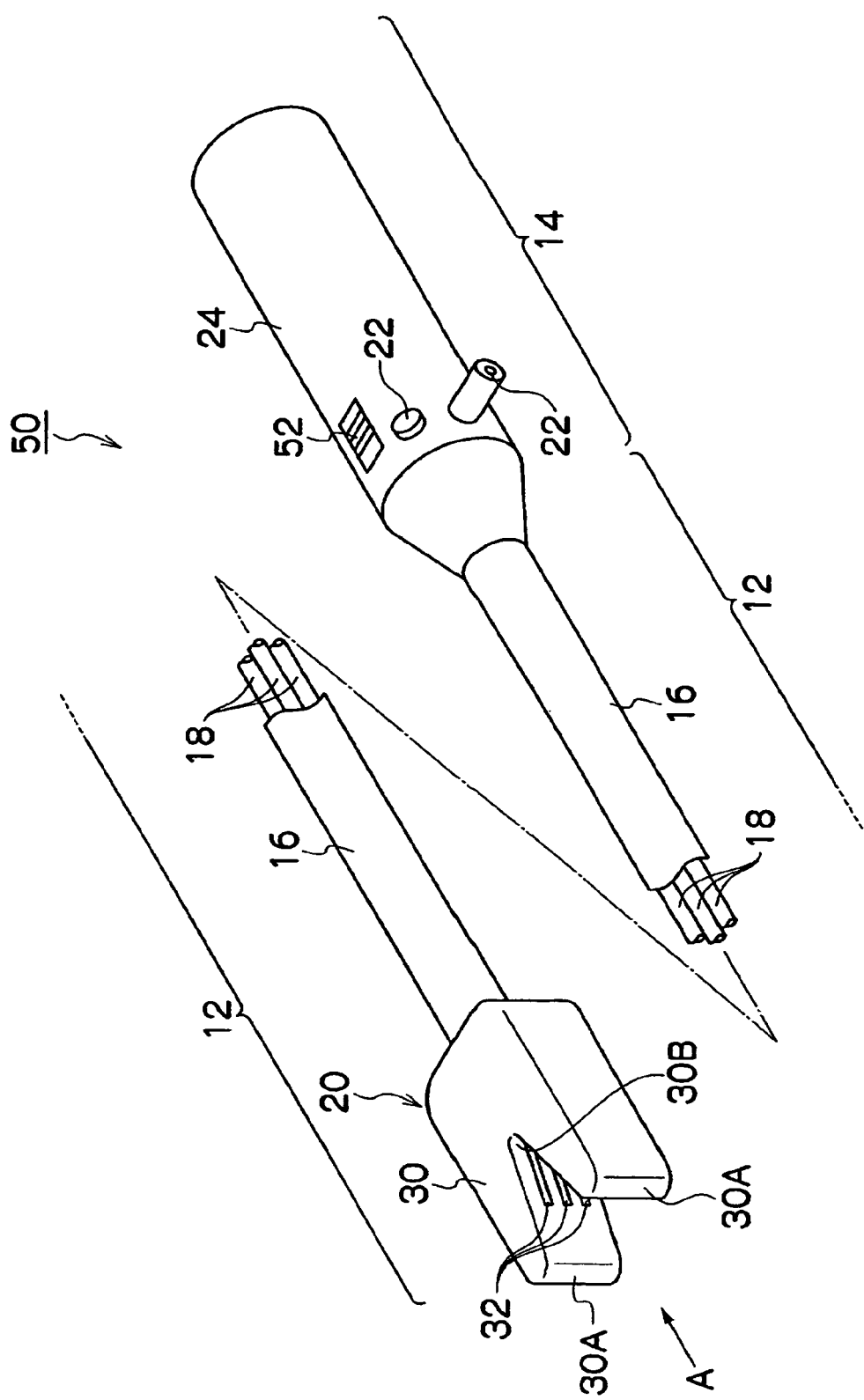
FIG. 7 is an oblique perspective view that illustrates a second embodiment of the treatment instrument for an endoscope relating to the present invention.
Figure 8:
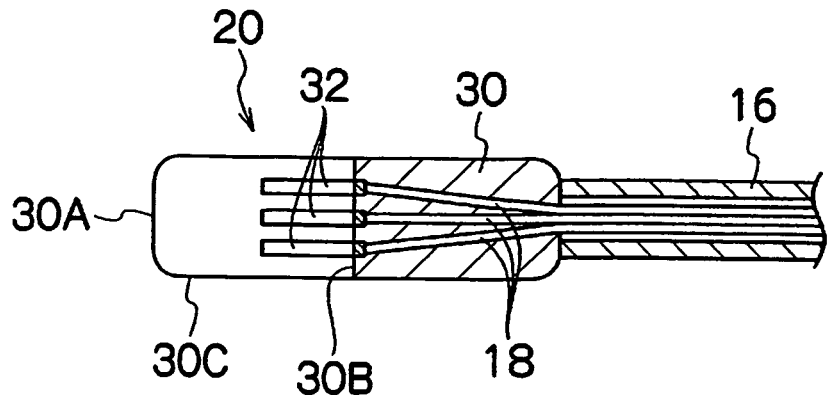
FIG. 8 is a sectional view that illustrates the treatment portion shown in FIG. 7.

Next, a treatment instrument for an endoscope according to the second embodiment is described using FIG. 7 and FIG. 8. FIG. 7 is an oblique perspective view that illustrates a treatment instrument for an endoscope according to the second embodiment. FIG. 8 is a lateral sectional view showing a treatment portion thereof. In this connection, although an example is shown in FIG. 7 and FIG. 8 in which a cutting portion (peak portions, valley portion and electrode plate) is only provided on the distal end side, a cutting portion of the same configuration as that on the distal end side can also be provided on the proximal end side. However, a configuration in which the cutting portion is only provided on the distal end side as shown in FIG. 7 and FIG. 8 and a configuration (not shown) in which the cutting portion is only provided on the proximal end side are also possible.

As shown in these drawings, in a treatment instrument for an endoscope 50 according to the second embodiment, three electrode plates 32, 32, and 32 are provided in a valley portion 30B of a treatment portion 20. The electrode plates 32, 32, and 32 are parallelly disposed at different distances from the underside 30C of the main unit 30. The electrode plates 32, 32, and 32 are respectively connected to different wires 18, 18, and 18, and these three wires 18, 18, and 18 are connected to a changeover switch 52 of a hand-side operation portion 14. The changeover switch 52 is configured to alternatively connect one of the three wires 18, 18, and 18 to the connector 22. Hence, by operating the changeover switch 52, one of the electrode plates 32, 32, and 32 can be selected to feed a high frequency current thereto. The wires 18, 18, and 18 are covered with an outer coat of a non-conductive member or are disposed in a state in which they are separated with a non-conductive partition member so as not to short circuit.

In the treatment instrument for an endoscope 50 configured as described above, since it is possible to select one among the three electrode plates 32, 32, and 32 and feed a high frequency current, the cutting position can be selected in the thickness direction of the main unit 30 of the treatment portion 20. That is, according to the treatment instrument for an endoscope 50, the cutting depth can be adjusted in three stages, enabling dissection at a stable depth.

It is to be understood that although the three electrode plates 32, 32, and 32 are provided according to the second embodiment, the number of electrode plates 32 is not limited thereto, and a configuration may also be adopted in which two or four or more electrode plates 32 are provided and selected.

Figure 9:
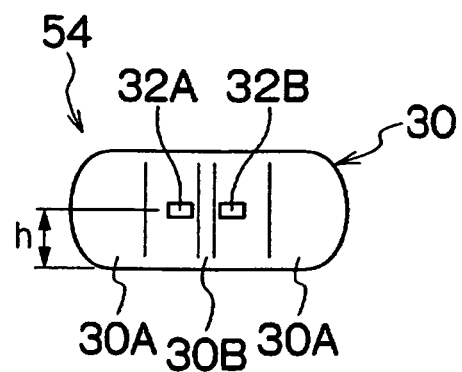
FIG. 9 is a front view that illustrates a treatment portion according to a third embodiment of the treatment instrument for an endoscope relating to the present invention.
Figure 10:
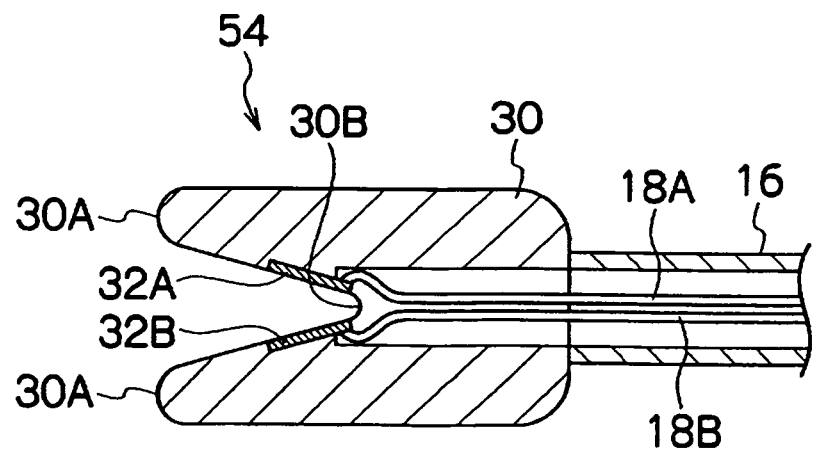
FIG. 10 is a sectional view of the treatment portion shown in FIG. 9.

Next, a treatment instrument for an endoscope according to the third embodiment is described using FIG. 9 and FIG. 10. FIG. 9 is a front view showing a treatment portion 54 according to the third embodiment, and FIG. 10 is a planar sectional view showing the treatment portion 54. In this connection, although an example is shown in FIG. 9 and FIG. 10 in which a cutting portion (peak portions, valley portion and electrode plate) is only provided on the distal end side, a cutting portion of the same configuration as that on the distal end side can also be provided on the proximal end side. However, a configuration in which the cutting portion is provided only on the distal end side as shown in FIG. 9 and FIG. 10, and a configuration (not shown) in which the cutting portion is only provided on the proximal end side are also possible.

The treatment instrument for an endoscope according to the third embodiment is a bipolar type treatment instrument in which a pair of electrodes for feeding a high frequency current is provided in the treatment portion 54. That is, in the treatment portion 54, two electrode plates 32A and 32B are provided in the valley portion 30B of the main unit 30. As shown in FIG. 9, the electrode plates 32A and 32B are disposed at a predetermined distance h from the underside 30C of the main unit 30. Further, the two electrode plates 32A and 32B are, as shown in FIG. 10, opposingly disposed on the sides of the valley portion 30B, and wires 18A and 18B are electrically connected to the electrode plates 32A and 32B. The wires 18A and 18B are connected to the connector 22 of the hand-side operation portion 14 (see FIG. 1). By connecting an unshown high-frequency current supply unit to the connector 22, a high frequency current is passed through the two electrode plates 18A and 18B. The two wires 18A and 18B are covered with an outer coat of a non-conductive member or are disposed in a state in which they are separated with a non-conductive partition member so as not to short circuit.

In the treatment instrument for an endoscope configured as described above, body tissue is cut by feeding a high frequency current between the pair of electrode plates 32A and 32B. Therefore, since only fibrous submucosa 38 that enters the valley portion 30B is cut, there is no risk of cutting the mucosa 34 or the muscularis propria 36, and the submucosa 38 can be cut safely and quickly.

Further, since the above described treatment instrument for an endoscope is a bipolar type, a counter-electrode plate (not shown) that is attached to a subject is not required, there is little risk of perforation, and the influence of the high frequency current on peripheral sites is small.

In this connection, disposition of the two electrode plates 32A and 32B is not limited to that of the above described embodiment. For example, the two electrode plates 32A and 32B may also be parallelly disposed at different height (depth) positions.

Figure 11:
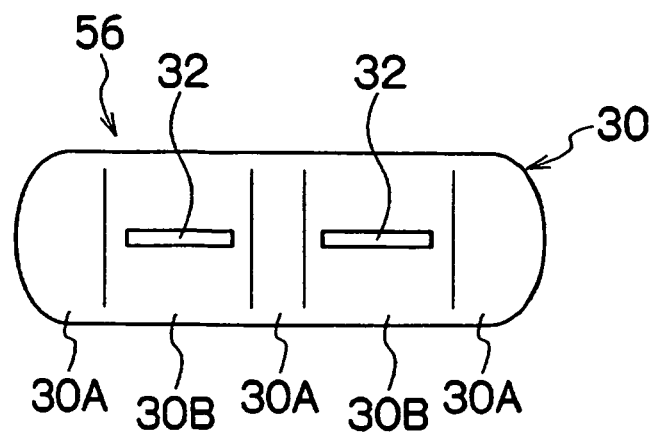
FIG. 11 is a front view that illustrates a treatment portion according to a fourth embodiment of the treatment instrument for an endoscope relating to the present invention.
Figure 12:
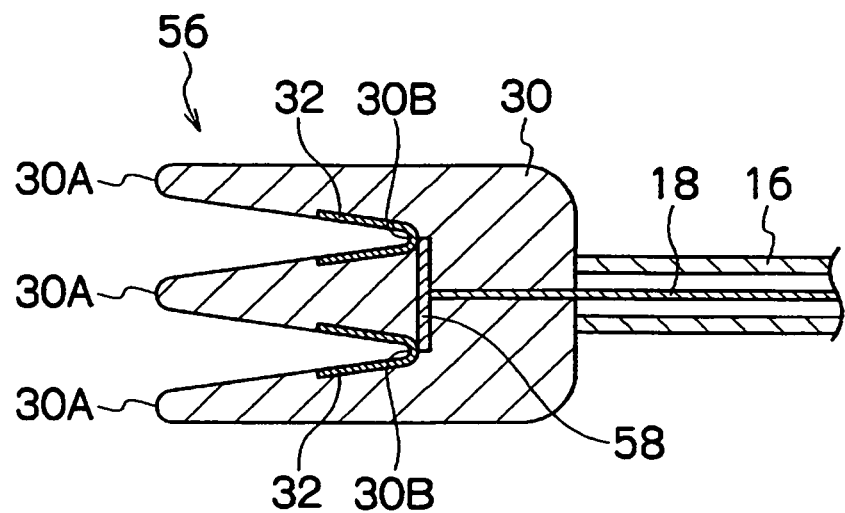
FIG. 12 is a sectional view of the treatment portion shown in FIG. 11.

Next, a treatment instrument for an endoscope according to the fourth embodiment is described using FIG. 11 and FIG. 12. FIG. 11 is a front view showing a treatment portion 56 according to the fourth embodiment, and FIG. 12 is a planar sectional view showing the treatment portion 56. In this connection, although an example is shown in FIG. 11 and FIG. 12 in which a cutting unit is provided only on the distal end side, a cutting portion of the same configuration (peak portions, valley portion and electrode plate) as that on the distal end side can also be provided on the proximal end side. However, a configuration in which the cutting portion is provided only on the distal end side as shown in FIG. 11 and FIG. 12 and a configuration (not shown) in which the cutting portion is only provided on the proximal end side are also possible.

The treatment portion 56 of the treatment instrument for an endoscope shown in these drawings is formed in a sawtooth shape in which the main unit 30 comprises three peak portions 30A, 30A, and 30A and two valley portions 30B and 30B, and respective electrode plates 32 and 32 are provided in the valley portions 30B and 30B. Each of the electrode plates 32 and 32 is electrically connected to a single wire 18 via a metal plate 58. The wire 18 is connected to the connector 22 of the hand-side operation portion 14 (see FIG. 1). Accordingly, by connecting a high-frequency current supply unit (not shown) to the connector 22, high frequency currents can be fed at the same time from both electrode plates 32 and 32.

In the treatment instrument for an endoscope configured as described above, since the submucosa 38 (see FIG. 6) can be simultaneously cut in the two valley portions 30B and 30B, the cutting area is increased and thus cutting of the submucosa 38 can be efficiently performed.

It is to be understood that the number of the valley portions 30B and 30B is not limited to one or to two, and three or more valley portions 30B may be provided with an electrode plate 32 disposed in each valley portion 30B. By providing a plurality of valley portions 30B in this manner, the cutting area is widened and cutting of the submucosa 38 can be performed more quickly. In a case in which a plurality of the valley portions 30B and 30B are provided, a configuration may be adopted in which the cutting depth can be selected by providing a plurality of the electrode plates 32 in each valley portion 30B as in the second embodiment, or a bipolar type configuration may be adopted in which both electrodes are provided in a single valley portion 30B.

Figure 13:
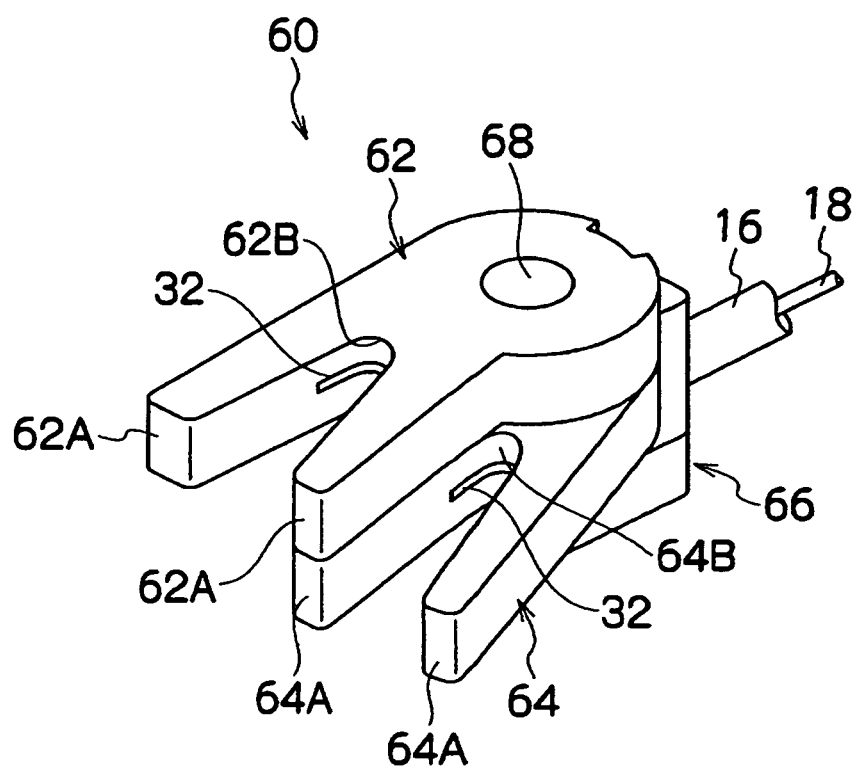
FIG. 13 is an oblique perspective view that illustrates a treatment portion according to a fifth embodiment of the treatment instrument for an endoscope relating to the present invention.
Figure 14:
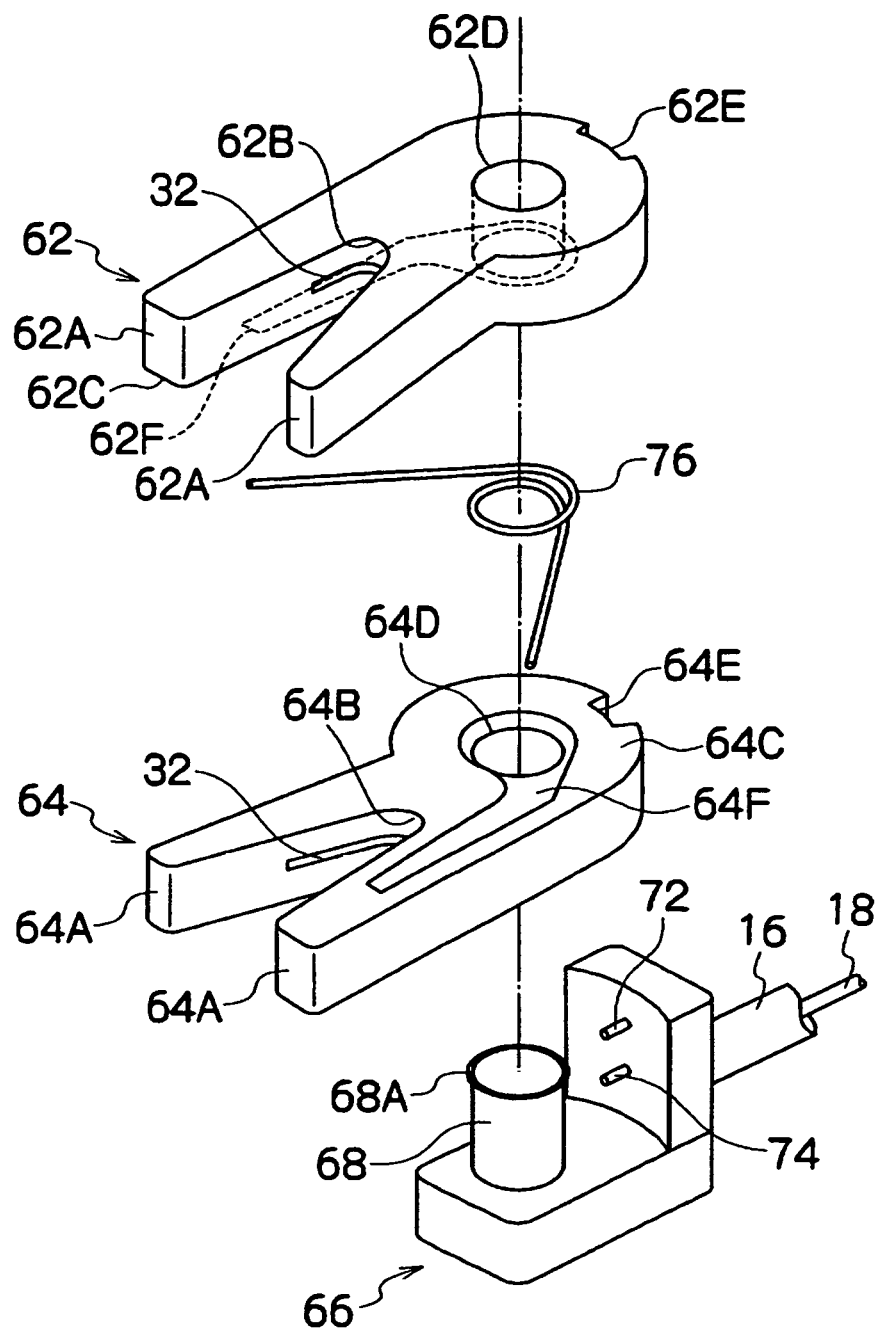
FIG. 14 is an exploded oblique perspective view illustrating the treatment portion shown in FIG. 13.

Next, a treatment instrument for an endoscope according to the fifth embodiment is described using FIG. 13 and FIG. 14. FIG. 13 is an oblique perspective view showing a treatment portion 60 according to the fifth embodiment, and FIG. 14 is an exploded oblique perspective view showing the treatment portion 60.

As shown in these drawings, the treatment portion 60 is principally composed by an upper piece 62, a lower piece 64, and a pedestal 66. The pedestal 66 is fixed to the tip of the flexible sheath 16. A shaft 68 that swingably supports the upper piece 62 and the lower piece 64 is provided in the pedestal 66. A flange 68A is provided on the top edge of the shaft 68. By engaging the flange 68A with the upper piece 62 that is described later, the upper piece 62 is stopped from falling out. Regulating pins 72 and 74 for regulating the swinging range of the upper piece 62 and the lower piece 64 are arranged in a standing condition in the pedestal 66.

The upper piece 62 is formed in a substantially V shape, and comprises peak portions 62A and 62A and a valley portion 62B. The electrode plate 32 is provided in the valley portion 62B. The electrode plate 32 is configured so as to be electrically connected to the wire 18 when the upper piece 62 is mounted on the pedestal 66. A hole 62D is provided in the upper piece 62. The shaft 68 of the pedestal 66 is inserted through the hole 62D to allow the upper piece 62 to be swingably supported by the pedestal 66. A regulating groove 62E is formed in the upper piece 62. The aforementioned regulating pin 72 is engaged with the regulating groove 62E to regulate the swinging range of the upper piece 62. A groove 62F is formed on an underside 62C of the upper piece 62, and a spring 76, described later, is arranged in the inside thereof.

Similarly to the upper piece 62, the lower piece 64 is formed in a substantially V shape, and comprises peak portions 64A and 64A and a valley portion 64B. The electrode plate 32 is provided in the valley portion 64B. The electrode plate 32 is configured so as to be electrically connected to the wire 18 when the lower piece 64 is mounted on the pedestal 66. A hole 64D is provided in the lower piece 64. The shaft 68 of the pedestal 66 is inserted through the hole 64D to allow the lower piece 64 to be swingably supported by the pedestal 66. A regulating groove 64E is formed in the lower piece 64. The aforementioned regulating pin 74 is engaged with the regulating groove 64E to regulate the swinging range of the lower piece 64. A groove 64F is formed on a top surface 64C of the lower piece 64, and the spring 76 is arranged inside the groove 64F. By arranging the spring 76 inside the groove 62F of the upper piece 62 and the groove 64F of the lower piece 64, the upper piece 62 and the lower piece 64 are urged in an extending direction as shown in FIG. 13.

In the treatment instrument for an endoscope configured as described above, the upper piece 62 and the lower piece 64 are swingably supported. Hence, by stacking the upper piece 62 and the lower piece 64, the treatment portion 56 can be made small, and thus the treatment portion 56 can be inserted through the forceps channel of the endoscope insertion portion 40 (see FIG. 5).

Further, since the upper piece 62 and the lower piece 64 are opened by the urging force of the spring 76 when the treatment portion 56 is led out from the forceps channel, the area for cutting by the electrode plates 32 and 32 widens and thus the cutting work can be performed efficiently.

Figure 22A:
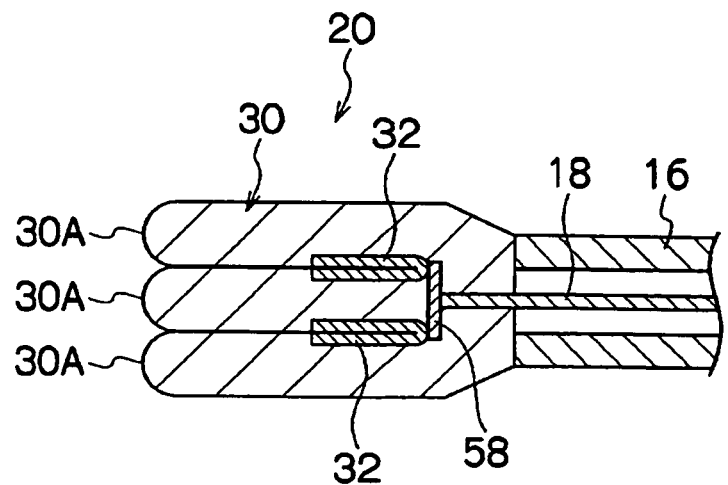
FIG. 22A is a view showing a state in which spaces between peak portions 30A, 30A, and 30A are narrowed.
Figure 22B:
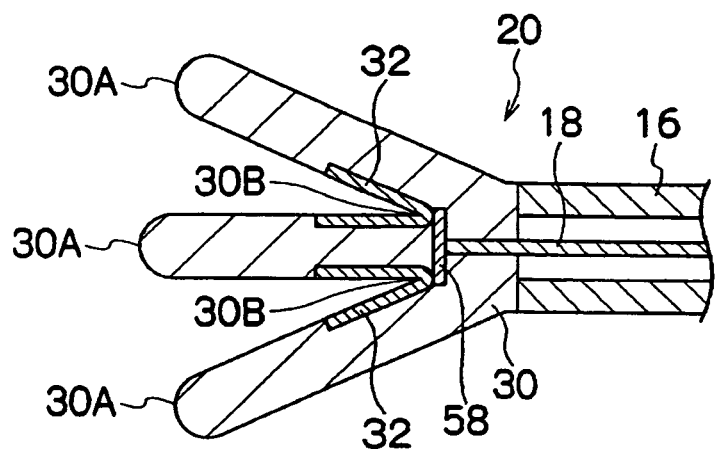
FIG. 22B is a view showing a state in which spaces between peak portions 30A, 30A, and 30A are widened.

Although the above described fifth embodiment is configured so that a space opens and closes between the peak portions by swinging the upper piece 62 and the lower piece 64, the above described embodiment is not limited to that configuration. For example, in a treatment portion 20 of a treatment instrument for an endoscope shown in FIGS. 22A and 22B, the main unit 30 is composed of a non-conductive rubber, the electrode plates 32 and 32 are composed of an electrically conductive rubber, and the electrode plates 32 and 32 are mounted on the main unit 30. In the main unit 30, in a state with no load, the spaces between the peak portions 30A, 30A, and 30A are open as shown in FIG. 22B. As shown in FIG. 22A, the main unit 30 can be elastically deformed so as to narrow the spaces between the peak portions 30A, 30A, and 30A. In this state the main unit 30 can be inserted through the forceps channel (not shown) of the endoscope. When the treatment portion 20 is led out from the forceps channel, the main unit 30 returns to its original shape as shown in FIG. 22B, and the spaces between the peak portions 30A, 30A, and 30A widen. Hence, since the valley portions 30B and 30B widen, cutting of the submucosa 38 can be performed in a wide range by the electrode plates 32 and 32.

In this connection, although in the above first to fifth embodiments the main unit 30 of the treatment portion 20 is formed in a sawtooth shape by aligning the peak portions 30A and valley portion 30B in a linear shape, the shape of the main unit 30 is not limited thereto, and the main unit 30 may be formed in a toothed-wheel shape by disposing the peak portions 30A and valley portion 30B in a circular shape. An embodiment employing this shape is described below.

Figure 15:
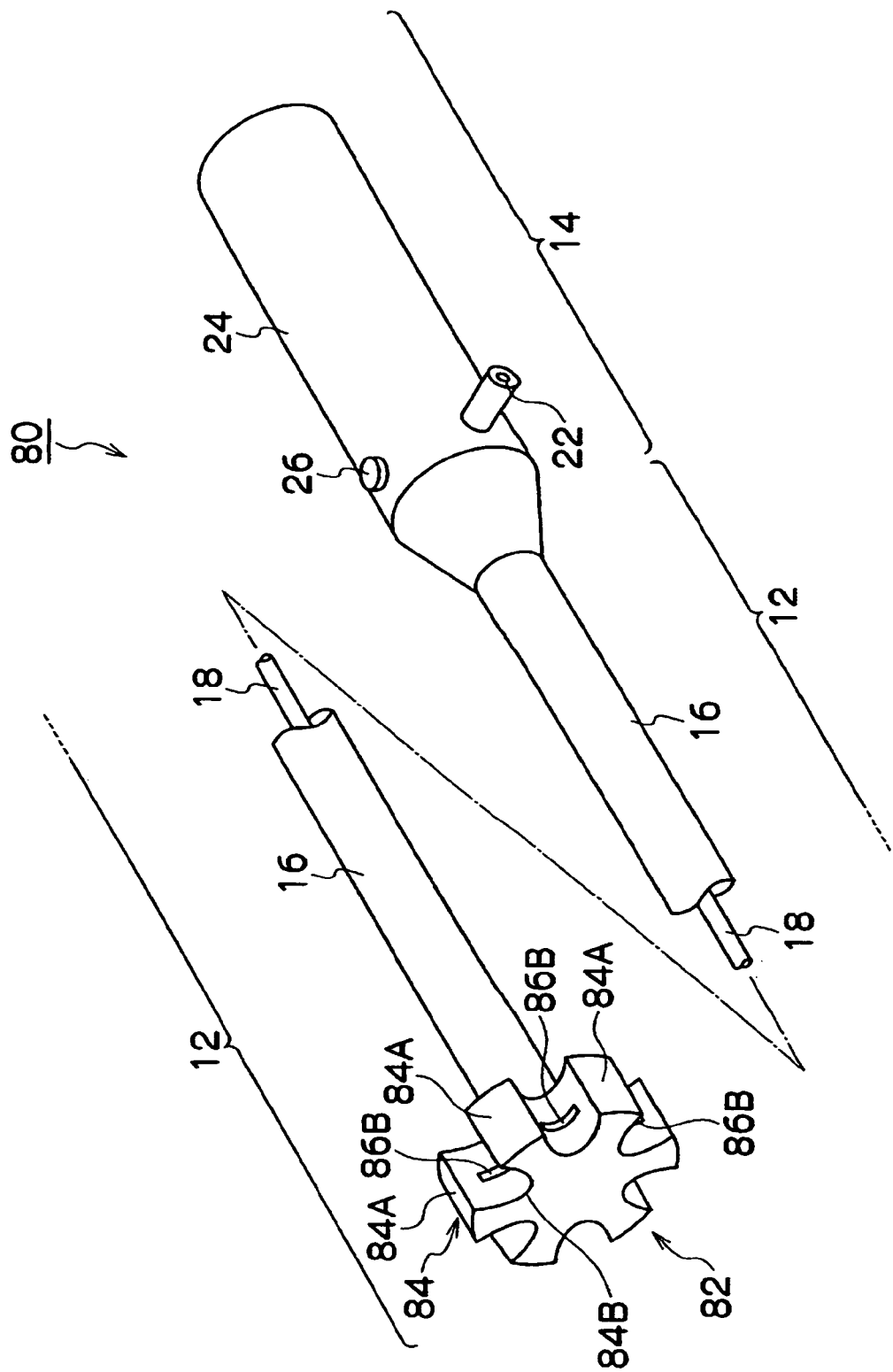
FIG. 15 is an oblique perspective view that illustrates a treatment portion according to a sixth embodiment of the treatment instrument for an endoscope relating to the present invention.
Figure 16:
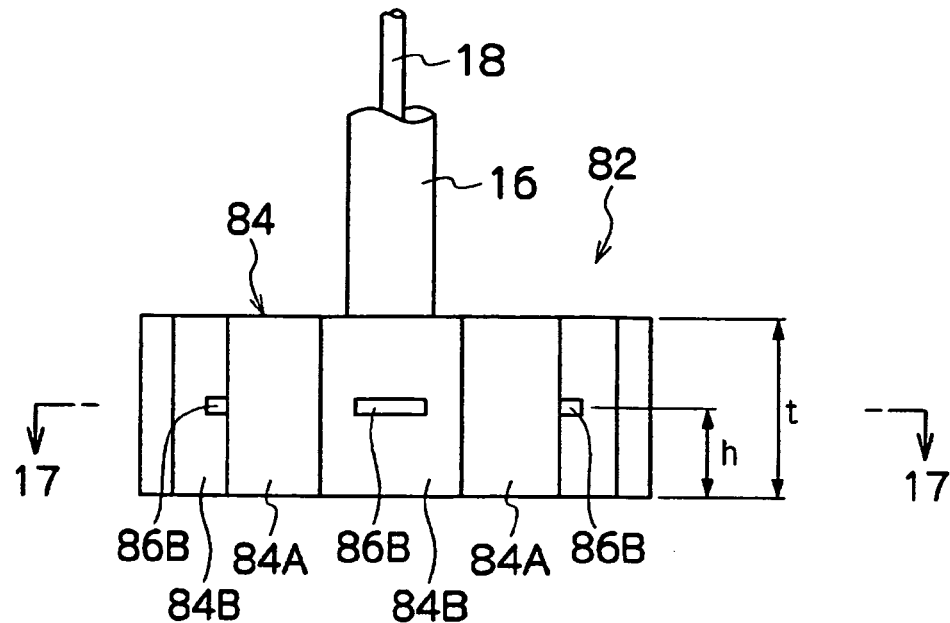
FIG. 16 is a side view of the treatment portion shown in FIG. 15.
Figure 17:
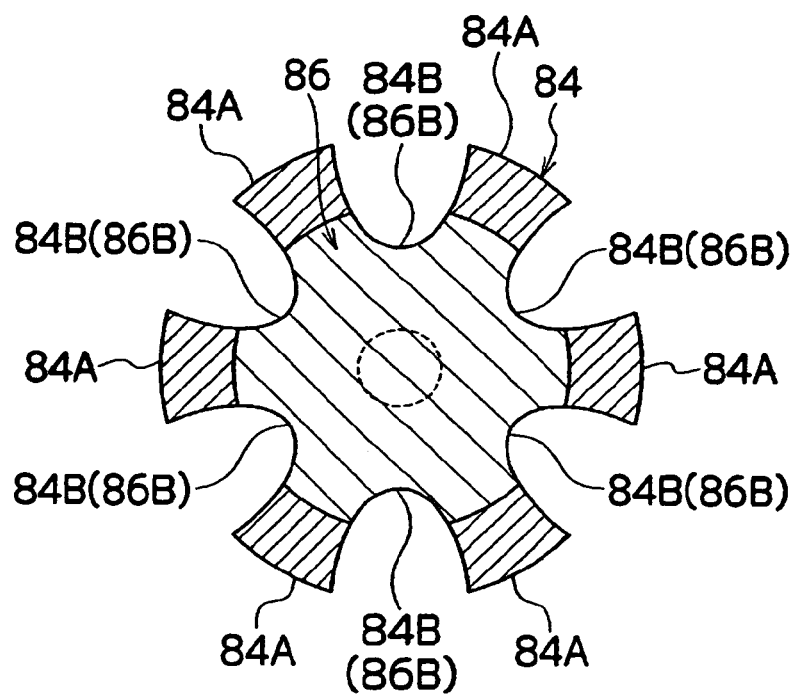
FIG. 17 is a sectional view along the line 17-17 of the treatment portion shown in FIG. 16.

FIG. 15 is an oblique perspective view illustrating a treatment instrument for an endoscope 80 according to the sixth embodiment. FIG. 16 is a side view of the treatment portion 82. FIG. 17 is a sectional view of the treatment portion 82 along a line 17-17 shown in FIG. 16.

As shown in these figures, a main unit 84 of a treatment portion 82 is attached to the tip of the flexible sheath 16. The main unit 84 of the treatment portion 82 is formed in a toothed-wheel shape. On the outer circumferential surface of the main unit 84 a plurality of U-shaped or V-shaped valley portions (grooves) 84B are formed at constant intervals. That is, on the outer circumferential surface of the main unit 84, peak portions 84A and valley portions 84B are repeatedly formed in alternating order. An electrode portion 86B comprising an electric conductor such as a metal or the like is provided in each valley portion 84B. As shown in FIG. 17, the electrode portion 86B is composed by a single metal plate 86 that is embedded into the inside of the main unit 84. One portion of the metal plate 86 is exposed to the outside at the valley portion 82B to thereby form the electrode portion 86B. The metal plate 86 is electrically connected to a wire 18. The wire 18 is inserted through the flexible sheath 16 and connected to the connector 22 of the hand-side operation portion 14. Hence, by connecting an unshown high-frequency current supply unit to the connector 22, a high frequency current can be passed through each electrode portion 86B.

As shown in FIG. 16, the electrode portion 86B is disposed at a predetermined distance h from a bottom surface 84C of the main unit 84 so that the electrode portion 86B does not contact against the muscularis propria 36 when the bottom surface 84C is contacted against the muscularis propria 36 (see FIG. 6). In this connection, a configuration may be adopted in which the electrode portions 86B, 86B . . . are configured by individually arranging an electric conductor in each valley portion 84B.

Figure 18:
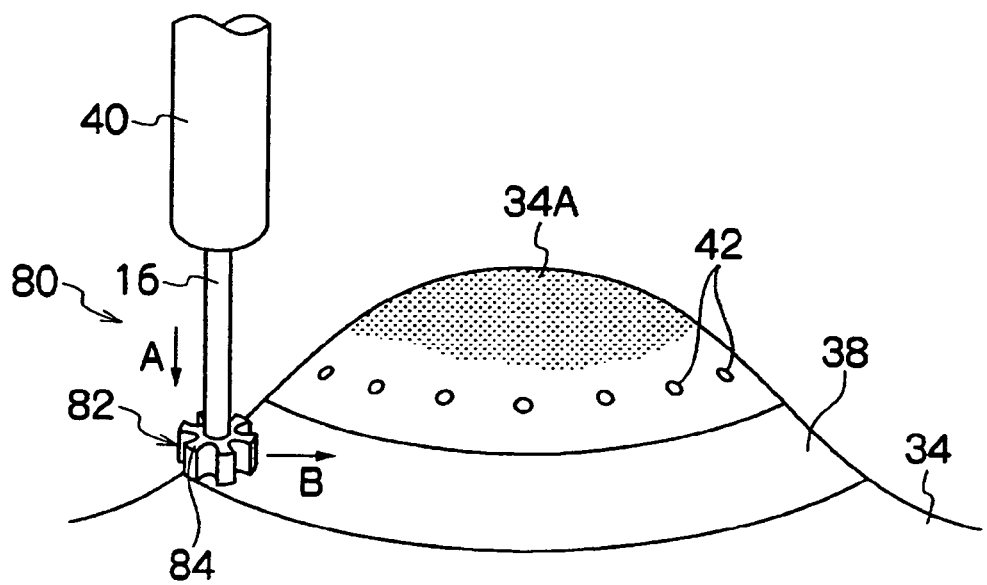
FIG. 18 is an explanatory view that describes a method of operating the treatment instrument for an endoscope shown in FIG. 15.

As shown in FIG. 18, in the treatment instrument for an endoscope 80 configured as described above, by leading the treatment portion 82 out from the forceps channel of the endoscope insertion portion 40 and pushing the treatment portion 82 in the direction in which the treatment portion 82 is led out (arrow A direction), the treatment portion 82 approaches the post-incision submucosa 38. Subsequently, the treatment portion 82 is moved in the diameter direction (arrow B direction) of the main unit 84 together with the endoscope insertion portion 40. Thus, the peak portions 84A, 84A . . . of the main unit 84 enter into the fiber of the submucosa 38 and the fiber of the submucosa 38 is collected in the valley portions 84B, 84B . . . . When the fiber of the submucosa 38 is touched by the electrode portions 86B of the valley portions 84B, a high frequency current concentrates at and flows to the submucosa 38 to perform cutting.

Thus, the treatment instrument for an endoscope 80 can easily cut the submucosa 38 by merely moving the treatment portion 82 in the diameter direction of the main unit 84. At that time, since the treatment portion 82 is always disposed at the front of the endoscope insertion portion 40, the cutting work can be constantly observed with the endoscope and thus the operations can be easily performed.

Further, in the treatment instrument for an endoscope 80, since the electrode portion 86B is provided in the valley portion 84B of the main unit 84, it is possible to cut only the submucosa 38 that is fiber. That is, in the case of the mucosa 34 or the muscularis propria 36 which are not fibers, since the mucosa 34 or the muscularis propria 36 do not contact against the peak portions 84A, 84A . . . and do not enter the valley portions 84B and 84B, there is no risk of damaging the mucosa 34 or muscularis propria 36 by the electrode portion 86B. Further, in the treatment instrument for an endoscope 80, since the electrode portion 86B is disposed at a predetermined distance h from the underside 84C of the main unit 84, even when the underside 84C of the main unit 84 contacts against the muscularis propria 36, there is no risk that the muscularis propria 36 will be cut. Accordingly, according to the treatment instrument for an endoscope 80, only the submucosa 38 can be cut safely and quickly.

Further, since the treatment instrument for an endoscope 80 is pushed out from the forceps in the direction in which it is being led to approach the submucosa 38, the approach to the cutting section is easy and the operability is favorable.

In this connection, the above described treatment instrument for an endoscope 80 may also be configured so that the cutting depth can be adjusted as in the second embodiment or may be configured as a bipolar type treatment instrument.

Figure 23A:
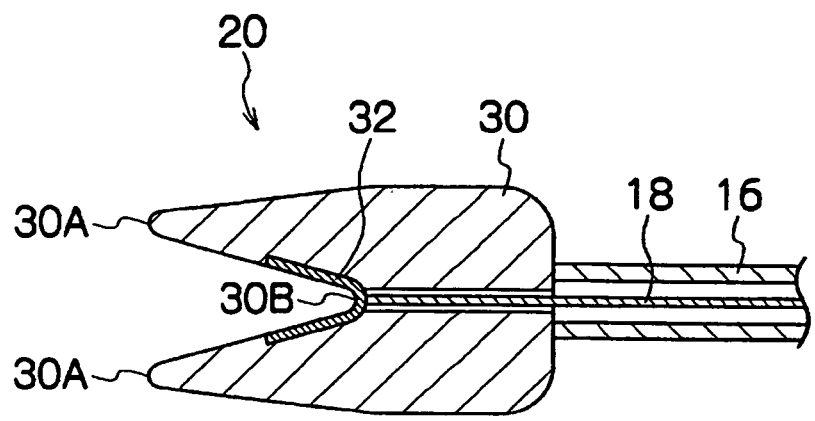
FIG. 23A is a planar sectional view of the treatment portion and FIG. 23B is a lateral sectional view of the treatment portion.
Figure 23B:
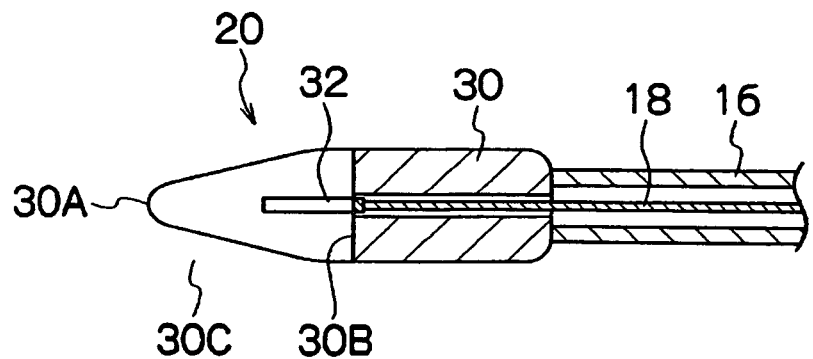

In this connection, although in the above described first to sixth embodiments the shapes of the peak portions 30A, 62A, 64A, and 84A are not particularly limited, a shape which is easy to insert into the fibrous submucosa 38 and that can prevent cutting of the muscularis propria 36 is preferable. For example, in FIG. 23A and FIG. 23B, the peak portions 30A and 30A on the distal end side are formed in a substantially conical tapered shape that narrows towards the tip, and the tip of the peak portions 30A and 30A is formed in a rounded shape to have a non-incisional property. As a result, the peak portions 30A and 30A are easily inserted into the submucosa 38 that is fibrous, and damage to the muscularis propria 36 when the peak portions 30A and 30A push against the muscularis propria 36 can be prevented. Although FIG. 23A and FIG. 23B illustrate an example in which a cutting unit is provided on only the distal end side, preferably a cutting unit having the same configuration is also provided on the proximal end side. That is, it is sufficient to form the peak portions 30D and 30D (see FIG. 3 and FIG. 4) on the proximal end side in a substantially conical tapered shape that narrows towards the tip, and form the tips in a rounded shape to achieve a non-incisional property. The same configuration can also be adopted when providing a cutting unit on only the proximal end side.

Figure 24A:
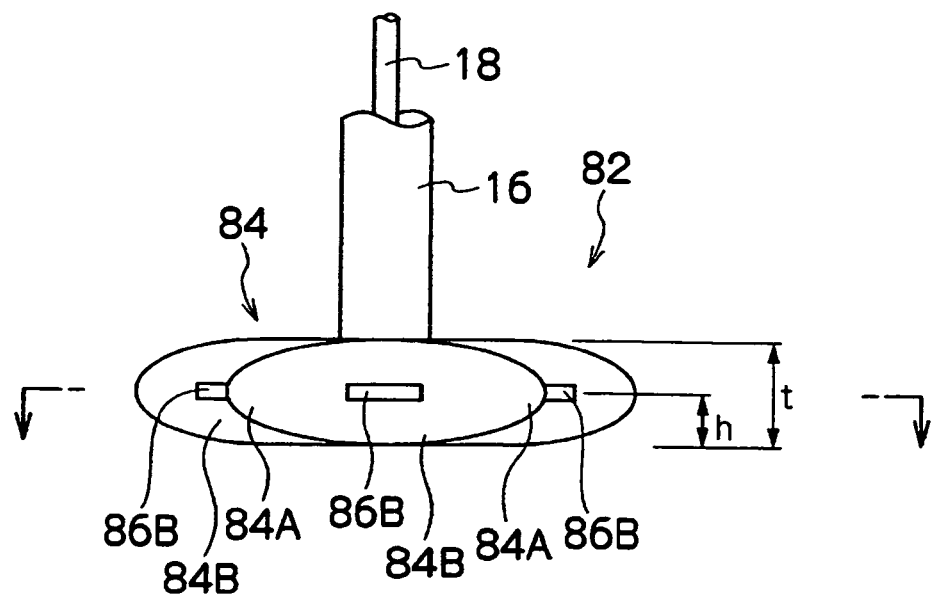
FIG. 24A is a side view of the treatment portion and FIG. 24B is a planar sectional view of the treatment portion.
Figure 24B:
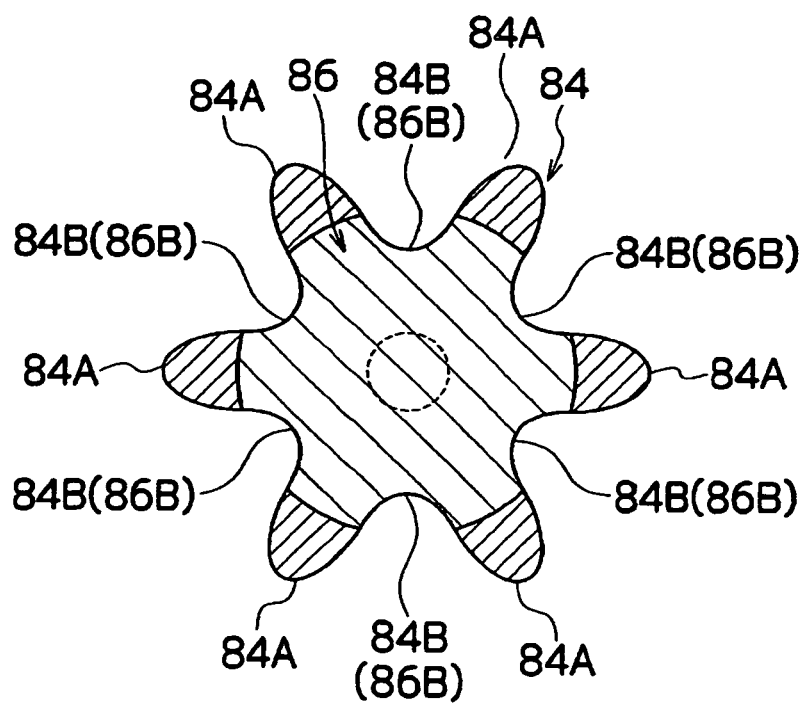

Similarly, the peak portions 84A and 84A shown in FIG. 16 and FIG. 17 may be formed as shown in FIG. 24A and FIG. 24B. The peak portions 84A and 84A shown in FIG. 24A and FIG. 24B are formed in a substantially conical tapered shape that narrows towards the tip, and the tips thereof are formed in a rounded shape to have a non-incisional property. As a result, the peak portions 84A and 84A are easily inserted into the submucosa 38 that is fibrous, and damage to the muscularis propria 36 when the peak portions 84A and 84A push against the muscularis propria 36 can be prevented.

Figure 25:
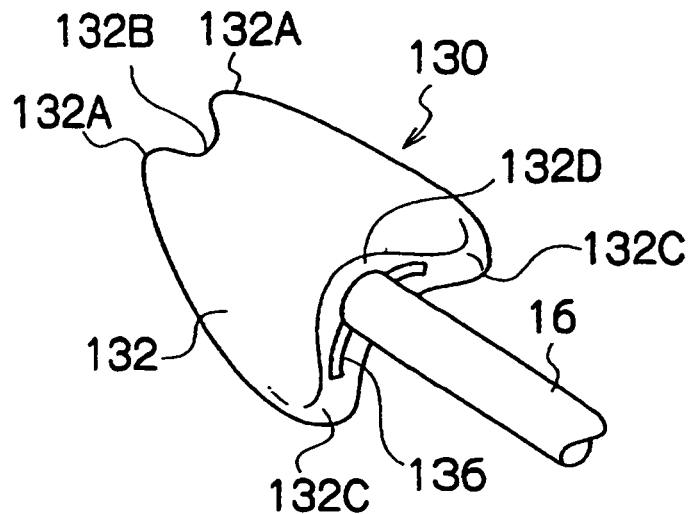
FIG. 25 is an oblique perspective view illustrating a treatment portion according to a seventh embodiment of the treatment instrument for an endoscope according to the present invention.
Figure 26:
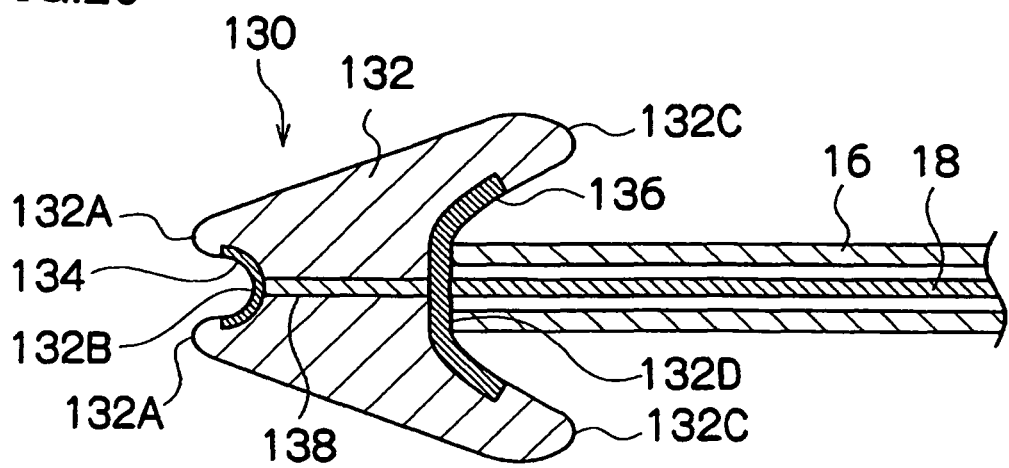
FIG. 26 is a planar sectional view of the treatment portion shown in FIG. 25.
Figure 27:
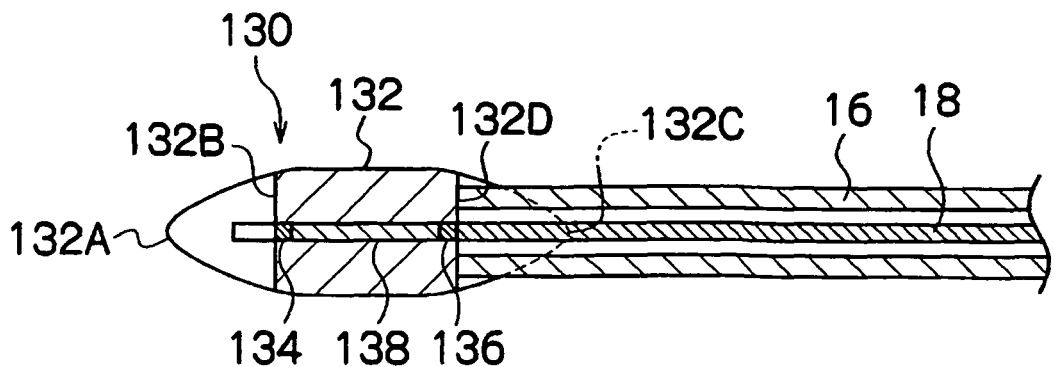
FIG. 27 is a lateral sectional view of the treatment portion shown in FIG. 25.
Figure 28:
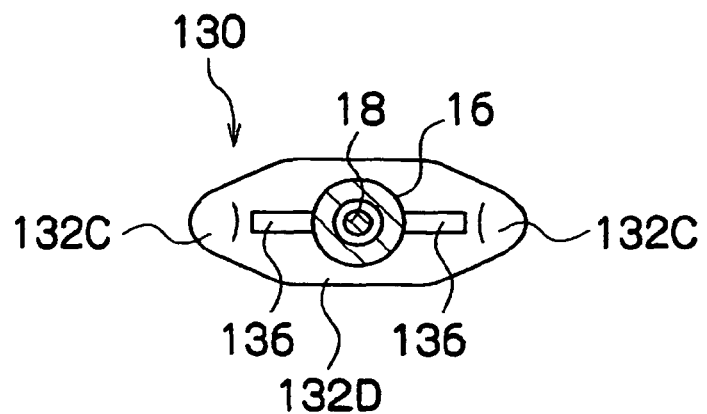
FIG. 28 is a rear view of the treatment portion shown in FIG. 25.
Figure 29:
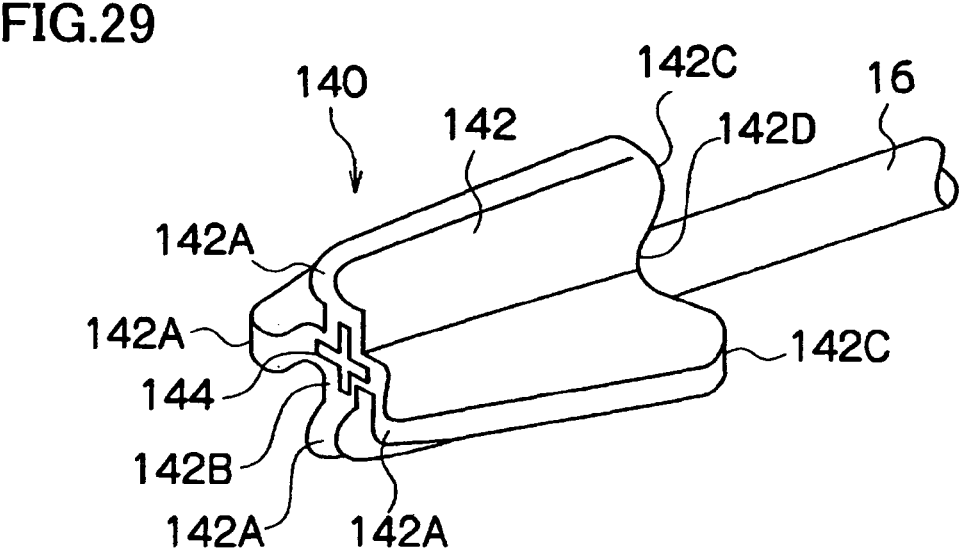
FIG. 29 is an oblique perspective view illustrating a treatment portion according to an eighth embodiment of the treatment instrument for an endoscope relating to the present invention.

Next, a treatment instrument for an endoscope according to the seventh embodiment is described based on FIG. 25 to FIG. 28. FIG. 25 to FIG. 27 are, respectively, an oblique perspective view, a planar sectional view, and a lateral sectional view that illustrate a treatment portion 130 according to the seventh embodiment. FIG. 28 is rear view showing the treatment portion 130 as viewed from the proximal end direction.

The treatment portion 130 according to the seventh embodiment shown in these figures is provided with cutting units on the distal end side and the proximal end side, respectively, of a non-conductive main unit 132. That is, an electrode plate 134 is provided on the distal end side of the main unit 132 and an electrode plate 136 is provided on the proximal end side of the main unit 132.

The main unit 132 of the treatment portion 130 comprises two peak portions 132A and 132A on the distal end side, a valley portion 132B formed between the peak portions 132A and 132A, two peak portions 132C and 132C on the proximal end side, and a valley portion 132D formed between the peak portions 132C and 132C. A space between the peak portions 132A and 132A on the distal end side is formed to be smaller than a space between the peak portions 132C and 132C on the proximal end side. In the overall main unit 132, the distal end side is formed to be smaller than the proximal end side. The size of the main unit 132 is substantially smaller than the internal dimensions of the forceps channel of an endoscope so that the main unit 132 can be inserted through the forceps channel of the endoscope.

The peak portion 132A and the peak portion 132C are formed in a substantially conical tapered shape that gradually narrows towards the tip as shown in the planar view of FIG. 26 and the side view of FIG. 27, and the tips thereof are rounded to have a non-incisional property. It is therefore possible to smoothly insert the peak portion 132A or peak portion 132C into the fibrous submucosa 38 and to prevent the muscularis propria 36 being cut when the peak portions 132A and 132C push against the muscularis propria 36.

Electrode plates 134 and 136 are provided in the valley portion 132B and valley portion 132D, respectively. As shown in FIG. 27, the electrode plates 134 and 136 are provided at a substantially intermediate position in the thickness direction of the main unit 132, and are configured so that the muscularis propria 36 does not touch the electrode plates 134 and 136 when the muscularis propria 36 contacts the top or bottom surfaces of the main unit 132. As shown in FIG. 26, the electrode plates 134 and 136 are disposed inside the valley portions 132B and 132D, that is, at positions that are separated from the top of the peak portion 132A and the top of the peak portion 132C so that the electrode plates 134 and 136 do not contact the muscularis propria 36 when the top of the peak portion 132A or the top of the peak portion 132C pushes against the muscularis propria 36. The electrode plate 134 and the electrode plate 136 are electrically connected by an electric conductor 138, and are also connected to the wire 18.

When the treatment portion 130 of the seventh embodiment configured as described above is to cut the submucosa 38, first the main unit 132 is moved to the distal end side to thereby push the main unit 132 into the submucosa 38. As a result, the peak portions 132A and 132A on the distal end side enter into the fibrous submucosa 38, whereby the submucosa 38 is collected in the valley portion 132B and contacts against the electrode plate 134. Thereby, a high frequency current flows to the submucosa 38 to cut the submucosa 38. Hence, the treatment portion 130 can be advanced to the distal end side while cutting the submucosa 38.

After the main unit 132 is completely pushed into the submucosa 38, the main unit 132 is moved to the proximal end side and a drawback operation is performed. As a result, the peak portions 132C and 132C on the proximal end side of the main unit 132 enter into the fibrous submucosa 38, whereby the submucosa 38 is collected in the valley portion 132D and contacts against the electrode plate 136. Thereby, a high frequency current flows to the submucosa 38 to cut the submucosa 38. Hence, the treatment portion 130 can be advanced to the proximal end side while cutting the submucosa 38.

Subsequently, a pushing and cutting operation is performed that cuts the submucosa 38 while advancing the treatment portion 130 to the distal end side again. Thereafter, a pulling and cutting operation is performed that cuts the submucosa 38 while drawing back the treatment portion 130 to the proximal end side. By repeating the pushing and cutting operation and pulling and cutting operation in this manner, the submucosa 38 is cut. Thus, according to the seventh embodiment, since the submucosa 38 is cut when the treatment portion 130 is both pushed in and pulled back, cutting of the submucosa 38 can be quickly performed.

In particular, according to the seventh embodiment, since the submucosa 38 is cut while pulling back the treatment portion 130, it is easy to apply force to the submucosa 38 and the submucosa 38 can be reliably cut. Further, since cutting is performed on the proximal end side of the treatment portion 130 when cutting while pulling back the treatment portion 130, operations can be performed while observing the cutting section from the observation optical system of the endoscope.

Although in the above described seventh embodiment the cutting units are provided on both the distal end side and the proximal end side of the treatment portion 130, the cutting unit may be provided on only the proximal end side. More specifically, in the treatment instrument shown in FIG. 25 to FIG. 28, it is sufficient to form the distal end side of the main unit 132 in a tapered shape that decreases in size as it approaches the distal end side and to form the tip thereof in a rounded shape. In that case, the submucosa 38 can be cut by drawing back the main unit 132 after moving the main unit 132 to the distal end side and pushing the main unit 132 into the fibrous submucosa 38. A configuration may also be adopted in which a cutting unit is provided only on the distal end side in the above described seventh embodiment. In this case, preferably the proximal end side is formed in a shape that does not cause a large resistance when pulling back the main unit 132.

Next, a treatment instrument for an endoscope according to the eighth embodiment is described based on FIG. 29 to FIG. 32. FIG. 29 to FIG. 32 are, respectively, an oblique perspective view, a planar sectional view, a front view from the distal end side, and a rear view from the proximal end side that illustrate a treatment portion 140 according to the eighth embodiment.

In the treatment portion 140 according to the eighth embodiment that is illustrated in these drawings, a non-conductive main unit 142 is formed in a shape in which four plate members are combined in a cross shape. That is, the main unit 142 is formed in a cross shape in which four plate members are disposed at intervals of 90° and are connected at the central axis side of the treatment portion 140.

On the distal end side of the main unit 142 four peak portions 142A, 142A . . . are formed by the outer peripheral section of each plate member protruding to the distal end side. A valley portion 142B is formed between the peak portions 142A, 142A . . . , i.e. in the central section. Similarly, on the proximal end side of the main unit 142 four peak portions 142C, 142C . . . are formed by the outer peripheral section of each plate member protruding to the proximal end side. A valley portion 142D is formed between these peak portions 142C, 142C . . . .

Figure 31:
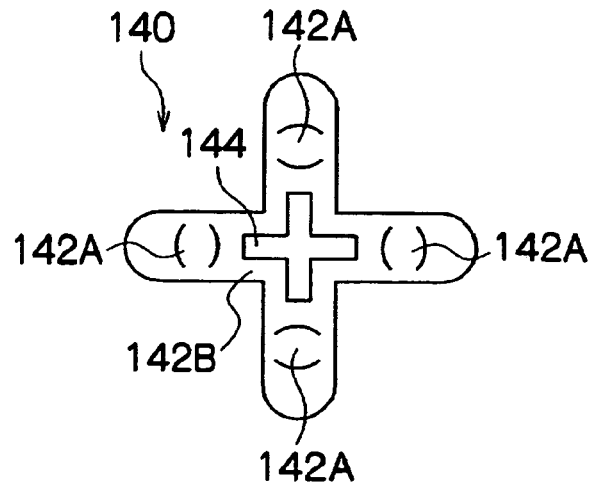
FIG. 31 is a front view of the treatment portion shown in FIG. 30.

As shown in FIG. 31, a cross-shaped electrode plate 144 is provided in the valley portion 142B on the distal end side. The electrode plate 144 is disposed at a position that is separated from the top of each peak portion 142A. The treatment portion 140 is configured so that the electrode plate 144 does not contact the muscularis propria 36 even when the peak portion 142A contacts the muscularis propria 36.

Figure 30:
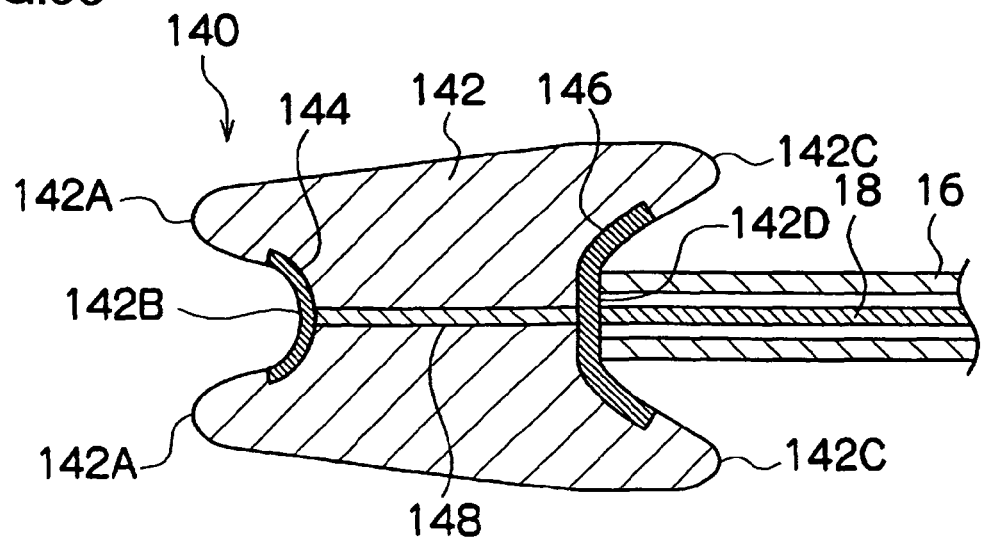
FIG. 30 is a planar sectional view of the treatment portion shown in FIG. 30.
Figure 32:
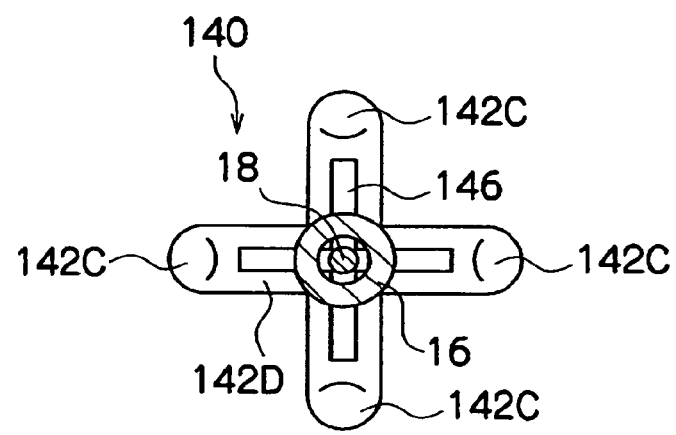
FIG. 32 is a rear view of the treatment portion shown in FIG. 31.

Similarly, as shown in FIG. 32, a cross-shaped electrode plate 146 is provided in the valley portion 142D on the proximal end side. The electrode plate 146 is disposed at a position that is separated from the top of each peak portion 142C. The treatment portion 140 is configured so that the electrode plate 146 does not contact the muscularis propria 36 even when the peak portion 142C contacts the muscularis propria 36. As shown in FIG. 30, the electrode plate 144 and the electrode plate 146 are electrically connected by an electric conductor 148, and the electrode plate 146 is also electrically connected to the wire 18.

The main unit 142 is formed so that the distal end side is smaller than the proximal end side to make it easy to push the main unit 142 into the submucosa 38. Further, each of the peak portions 142A and 142C of the main unit 142 are formed to be smaller toward the distal end side, and the tips thereof are formed in a rounded shape to have a non-incisional property. Accordingly, it is easy to push the peak portion 142A or peak portion 142C into the fibrous submucosa 38, and damage to the muscularis propria 36 by the peak portion 142A or peak portion 142C can be prevented. Further, the size of the main unit 142 is substantially smaller than the internal dimensions of the forceps channel of an endoscope, and thus the main unit 142 can be inserted through the forceps channel of the endoscope without hindrance.

Similarly to the seventh embodiment, in the eighth embodiment configured as described above, the submucosa 38 is cut by repeatedly performing a pushing and cutting operation that cuts the submucosa 38 while advancing the treatment portion 140 to the distal end side and a pulling and cutting operation that cuts the submucosa 38 while drawing back the treatment portion 140 to the proximal end side. Accordingly, since the submucosa 38 is cut when the treatment portion 140 is both pushed in and pulled back, cutting of the submucosa 38 can be quickly performed.

Further, according to the eighth embodiment, since the electrode plates 144 and 146 are disposed in the center (central axis side) of the treatment instrument 140, even if the treatment instrument 140 rotates around the axis line, the electrode plates 144 and 146 are always disposed in the center. Accordingly, cutting of the submucosa 38 can be performed without affecting the posture of the treatment portion 140.

Although in the above described eighth embodiment the cutting units are provided on both the distal end side and the proximal end side of the treatment portion 140, the cutting unit may be provided on only the proximal end side. More specifically, it is sufficient to form the distal end side of the main unit 142 in a tapered shape that decreases in size as it approaches the distal end side and to form the tip thereof in a rounded shape.

Further, although in the above described eighth embodiment the main unit 142 is formed by combining four plate-shaped members, the number of plate-shaped members may be three or five or more. In any case, it is preferable to arrange the plate-shaped members at equiangular intervals.

Figure 33:
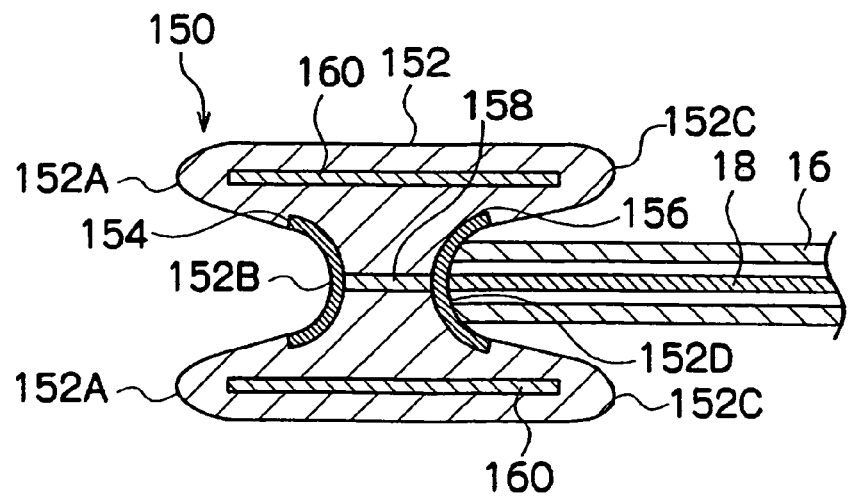
FIG. 33 is a planar sectional view illustrating a treatment portion according to a ninth embodiment of the treatment instrument for an endoscope relating to the present invention.
Figure 34:
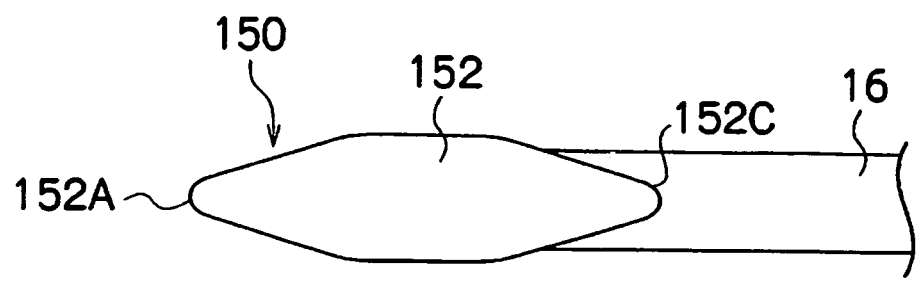
FIG. 34 is a side view of the treatment portion shown in FIG. 33.
Figure 35:
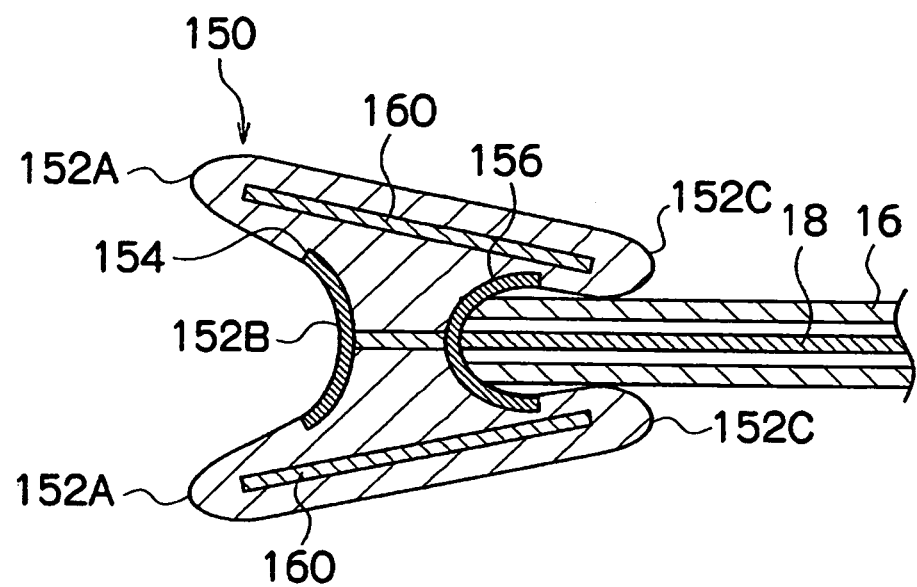
FIG. 35 is a planar sectional view showing a state after the treatment portion shown in FIG. 33 changed shape.
Figure 36:
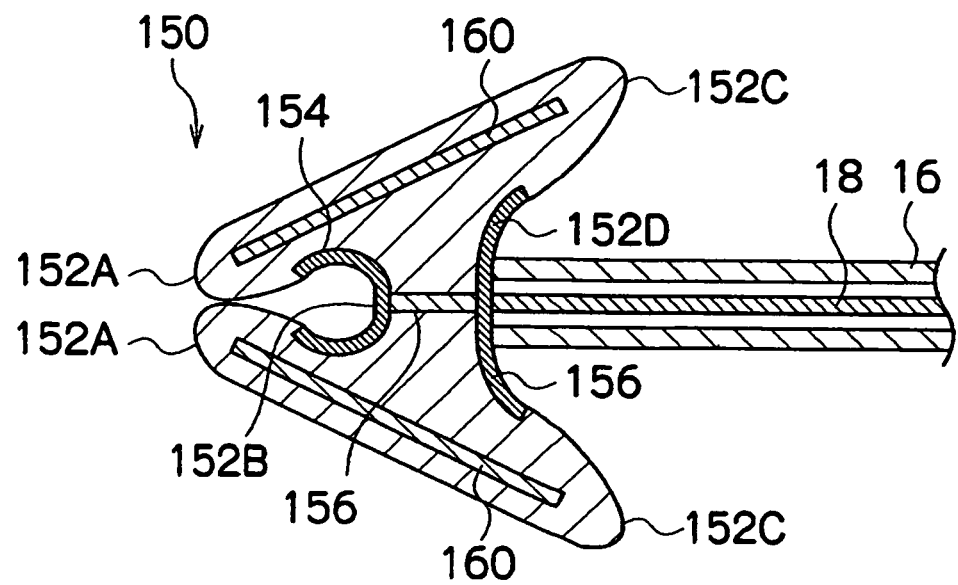
FIG. 36 is a planar sectional view showing a state after the treatment portion shown in FIG. 33 changed shape.

Next, a treatment instrument for an endoscope according to the ninth embodiment is described based on FIG. 33 to FIG. 36. FIG. 33 and FIG. 34 are, respectively, a planar sectional view and a side view that illustrate a treatment portion 150 according to the ninth embodiment. Further, FIG. 35 is a view showing the treatment portion 150 when it is moved to the distal end side and FIG. 36 is a view showing the treatment portion 150 when it is moved to the proximal end side.

In the treatment portion 150 shown in these drawings, a main unit 152 is formed in a shape of the Chinese character of "工" (or "H" shape) using an elastic member such as a non-conductive rubber. Accordingly, the main unit 152 has peak portions 152A and 152A on the distal end side and a valley portion 152B formed therebetween, as well as peak portions 152C and 152C on the proximal end side and a valley portion 152D formed therebetween. As shown in FIG. 33 and FIG. 34, each peak portion 152A and each peak portion 152C are formed in a tapered shape that narrows towards the tip, and the tips are rounded to have a non-incisional property.

Electrode elements 154 and 156 are provided in the valley portions 152B and 152D, respectively. The electrode elements 154 and 156 are arranged at a substantially intermediate position in the thickness direction of the main unit 152. Further, the electrode elements 154 and 156 are arranged so as not to engage with the top of the peak portion 152A or peak portion 152C. The electrode element 154 and the electrode element 156 are connected by an electric conductor 158. The electrode element 156 also connects to a wire 18. The electrode elements 154 and 156 are composed by an elastic member having electrical conductivity such as an electrically conductive rubber, and are configured so as to change shape elastically together with the main unit 152.

Rigid elements 160 and 160 are embedded inside the main unit 152. The rigid element 160 is disposed at a position that links the peak portion 152A on the distal end side and the peak portion 152C on the proximal end side. Accordingly, the main unit 152 comprising an elastic member is configured to change shape elastically at sections excluding the sections in which the rigid elements are disposed. More specifically, the main unit 152 is configured to change shape elastically so that the space between the peak portions 152A and 152A on the distal end side widens and the space between the peak portions 152C and 152C on the proximal end side narrows as shown in FIG. 35, or to change shape elastically so that the space between the peak portions 152A and 152A on the distal end side narrows and the space between the peak portions 152C and 152C on the proximal end side widens as shown in FIG. 36. In this connection, in the natural state, as shown in FIG. 33, the rigid elements 160 and 160 are parallel and the maximum outside diameter of the treatment portion 150 is at its smallest.

When the treatment portion 150 of the ninth embodiment configured as described above is advanced to the distal end side inside the submucosa 38, the submucosa 38 acts as a resistance so that the space between the peak portions 152A and 152A automatically widens as shown in FIG. 35. It is therefore possible to gather a wide region of the submucosa 38 in the valley portion 152B on the distal end side, and the submucosa 38 can be quickly cut by the electrode element 154 in the valley portion 152B.

Further, when the treatment portion 150 is advanced to the proximal end side inside the submucosa 38, the submucosa 38 on the proximal end side acts as a resistance so that the space between the peak portions 152C and 152C automatically widens as shown in FIG. 36. It is therefore possible to gather a wide region of the submucosa 38 in the valley portion 152D on the proximal end side, and the submucosa 38 can be quickly cut by the electrode element 156 in the valley portion 152D.

Further, according to the treatment portion 150 of the ninth embodiment, since the main unit 152 returns to the natural state shown in FIG. 34 after cutting, the maximum outside diameter of the main unit 152 decreases and the treatment portion 150 can be easily inserted through the forceps channel of the endoscope.

In the above described ninth embodiment, it is preferable to adopt a configuration whereby the maximum outside diameter of the treatment portion 150 can be fixed in its smallest state (i.e. the state shown in FIG. 33). For example, it is sufficient to provide a ring-shaped fitting member that fits onto the peak portions 152C and 152C from the proximal end side, to provide this fitting member in a slidable condition along the sheath 16, and to provide a slide operation unit of the fitting member in the hand-side operation portion 14. In this case, since the peak portions 152C and 152C of the treatment portion 150 can be fixed with the fitting member, the maximum outside diameter of the treatment portion 150 can be fixed in its smallest state, and the treatment portion 150 can be reliably inserted through the forceps channel of the endoscope.

Although in the above-described first to ninth embodiments, the treatment portions 20, 54, 56, 60, 82, 130, 140, and 150 are fixedly attached to the tip of the flexible sheath 16, the configurations are not limited thereto, and a configuration may be adopted in which the relevant treatment portion 20, 54, 56, 60, 82, 130, 140, or 150 is supported via a swivel mechanism.

Figure 19:
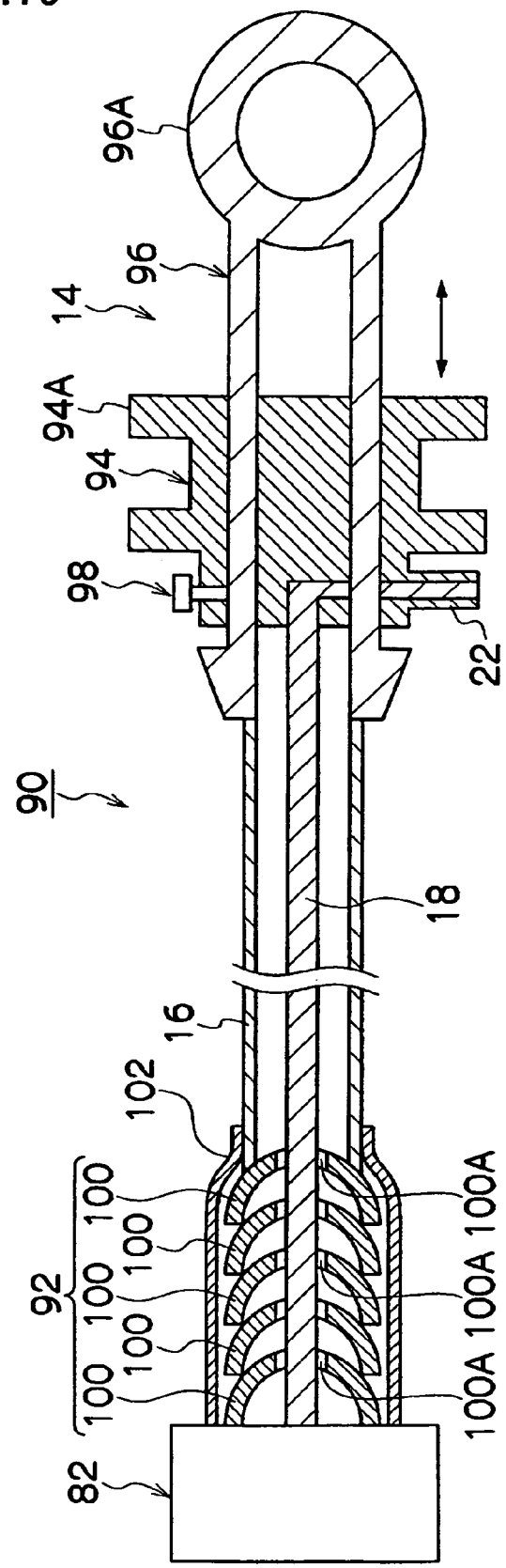
FIG. 19 is a sectional view illustrating a treatment instrument for an endoscope in which the treatment portion is swivelably supported.

FIG. 19 is a sectional view of a treatment instrument for an endoscope 90 in which a bending portion 92 (swivel mechanism) is provided between the treatment portion 82 and the flexible sheath 16.

As shown in the figure, the treatment portion 82 is supported via a bending portion 92 comprising a plurality of (for example, five) cup members 100, 100 . . . . A hole 100A is formed in each cup member 100. The wire 18 is inserted through the holes 100A. The tip of the wire 18 is fixed to a main unit 84 of the treatment portion 82, and the proximal end of the wire 18 is coupled to a slider 94 of a hand-side operation portion 14. The slider 94 is slidably supported by the main unit 96 of the hand-side operation portion 14. Locking and unlocking of the slider 94 with the main unit 96 is performed by operating a lock screw 98 provided in the slider 94. A flange 94A for engaging a forefinger and a middle finger of the technician is formed in the slider 94, and a ring portion 96A for engaging a thumb of the technician is formed at the proximal end of the main unit 96.

The proximal end of the flexible sheath 16 is fixedly attached to the main unit 96 of the hand-side operation portion 14. The tip of the flexible sheath 16 is fixedly attached to the cup member 100 that is furthest on the proximal end side. The flexible sheath 16 has a moderate rigidity and the configuration is such that the flexible sheath 16 is not bent or crushed when the slider 94 is slid to the proximal end side to increase the tension of the wire 18.

The bending portion 92 is covered by a cover tube 102 comprising a flexible material such as rubber. The tip of the cover tube 102 is fixedly attached to the main unit 84 of the treatment portion 82. The proximal end of the cover tube 102 is attached to the proximal end of the flexible sheath 16.

Figure 20:
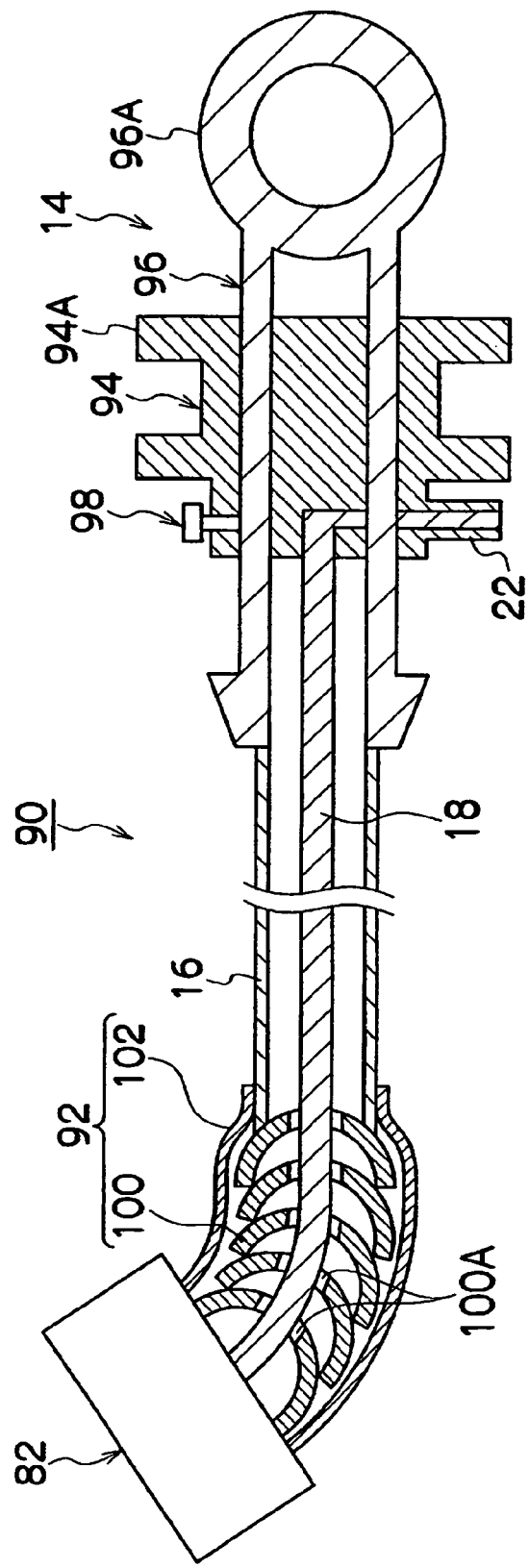
FIG. 20 is a sectional view showing a state in which a bending portion shown in FIG. 19 is bent.

In the treatment instrument for an endoscope 90 configured as described above, by sliding the slider 94 of the hand-side operation portion 14 to the distal end side with respect to the main unit 96, the tension of the wire 18 is decreased and the friction between the cup members 100 decreases. Hence, the bending portion 92 can be freely bent and, for example, the bending portion 92 can be bent as shown in FIG. 20.

Conversely, when the slider 94 is slid to the proximal end side of the main unit 96, the tension in the wire 18 increases to thereby increase friction between the cup members 100. Hence, the bending portion 92 is fixed in that shape. Accordingly, when the bending portion 92 has been bent, the bending portion 92 can be fixed as it is in that bent shape. By tightening the lock screw 98 in that state, the bent state can be retained.

According to the treatment instrument for an endoscope 90, since the bending portion 92 can be bent in this manner, the posture of the treatment portion 82 can be freely adjusted and fixed. As a result, the approach of the treatment portion 82 to the submucosa 38 is facilitated and work to cut the submucosa 38 can be easily performed.

Figure 21:
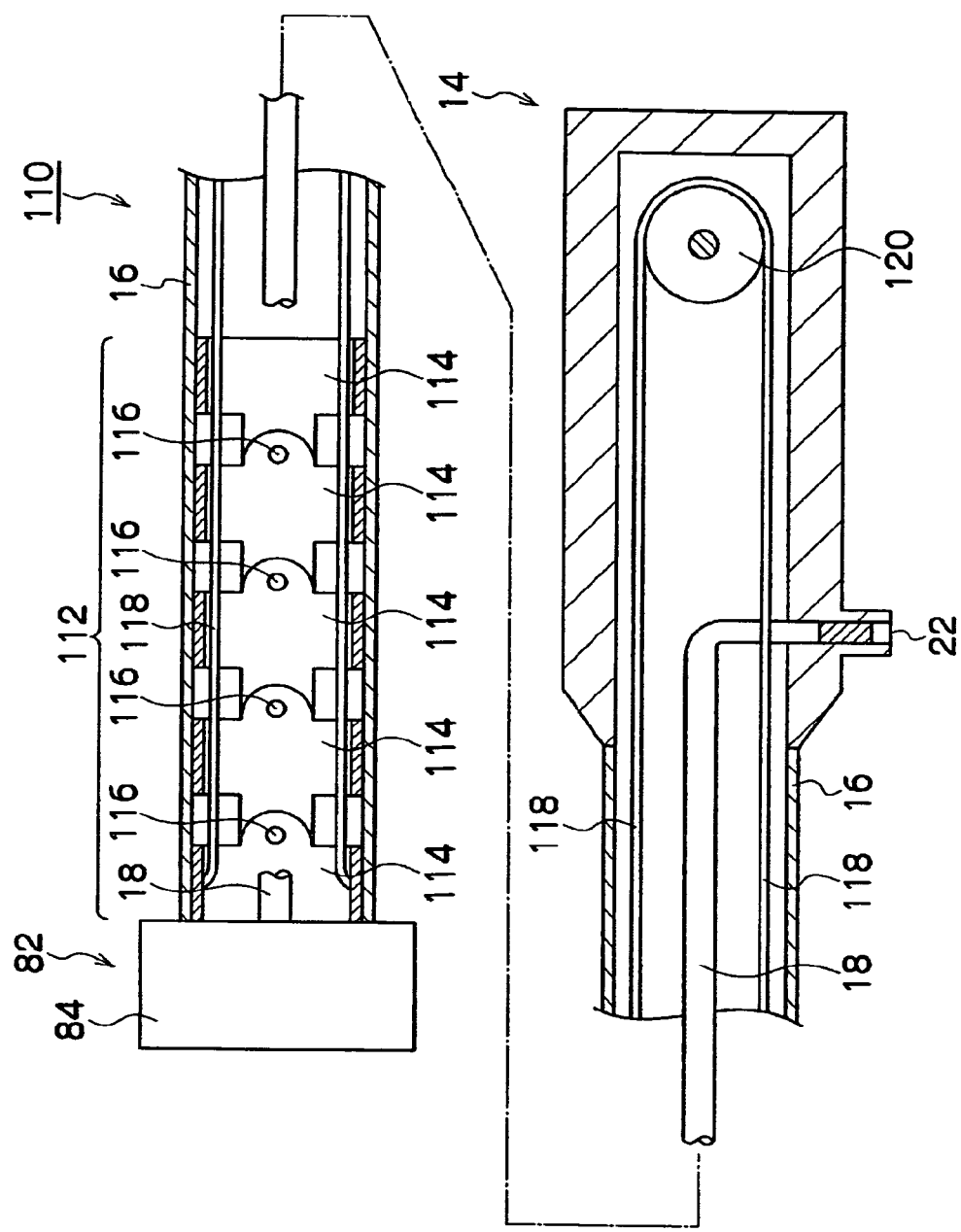
FIG. 21 is a sectional view showing a treatment instrument for an endoscope having a swivel mechanism with a different configuration to that shown in FIG. 19.

In this connection, a swivel mechanism of the treatment portions 20, 54, 56, 60, 82, 130, 140, and 150 is not limited to the above described embodiment and can be configured, for example, as shown in FIG. 21. In a treatment instrument for an endoscope 110 shown in FIG. 21, the treatment portion 82 is supported via a bending portion 112. The bending portion 112 has a plurality of cylindrical adjustment rings 114, 114 . . . . The adjustment rings 114 are rotatably connected together by pins 116. The adjustment ring 114 at the tip of the plurality of adjustment rings 114 is fixedly attached to the treatment portion 82, and the tips of operation wires 118 and 118 are fixed to the adjustment ring 114. The operation wires 118 and 118 are inserted through the inside of the flexible sheath 16 and wound over a pulley 120 of the hand-side operation portion 14. Hence, rotating the pulley 120 with a knob (unshown) or the like executes an operation to push or pull the operation wires 118 and 118, whereby the adjustment rings 114, 114 . . . rotate to cause the bending portion 112 to undergo a bending operation.

According to the treatment instrument for an endoscope 110 configured as described above, since the bending portion 112 can be freely bent, the posture of the treatment portion 82 can be freely adjusted. Accordingly, the approach of the treatment portion 82 to the submucosa 38 is facilitated and work to cut the submucosa 38 can be easily performed.

In this connection, although FIG. 21 illustrates a bending structure which can be bent in only two directions (up and down), the bending directions are not limited to these, and the structure may be one that can be bent in the four directions up, down, left, and right.

Further, the swivel mechanism of the treatment portions 20, 54, 56, 60, 82, 130, 140, and 150 may allow the treatment portion 82 to rotate by utilizing a rack and pinion or may support the treatment portion 82 with a linear member comprising a shape memory material to change the posture of the treatment portion 82 by electrifying and heating the linear member.

Although the cutting unit of the above described embodiment cuts by feeding a high frequency current, the kind of the cutting unit is not limited thereto, and a cutting unit may also be employed that uses a laser beam or ultrasonic waves. For example, the tip of an optical fiber is disposed at the position of the above described electrode plates 32, 33, 86B, 134, 136, 144, 146, 154, 156, the optical fiber is inserted through the flexible sheath 16, and the proximal end of the optical fiber is connected to an external laser beam oscillator. Thus, since a laser beam is irradiated at the submucosa 38 that entered the valley portion, the submucosa 38 can be cut with the laser beam. In this case, it is sufficient to provide a laser beam radiating unit inside the valley portion and on the side of one of the peak portions and radiate the laser beam towards the other peak portion side. It is thereby possible to reliably cut only the submucosa 38 that enters the valley portion. When using a cutting unit that employs ultrasonic waves, an ultrasonic transducer is disposed at the position of the above described electrode plates 32, 33, 86B, 134, 136, 144, 146, 154, and 156, and a conductor connected thereto is inserted through the inside of the flexible sheath 16 and connected to an external drive circuit. Thus, ultrasonic waves are transmitted towards the submucosa 38 that entered the valley portion to cut the submucosa 38 with the ultrasonic waves.

Further, in the above described first to ninth embodiments, preferably the size of the treatment portions 20, 54, 56, 60, 82, 130, 140, and 150 is made to be substantially smaller than the forceps channel of the endoscope so that the treatment portion in question can be inserted through the forceps channel of the endoscope. In this connection, the term "substantially smaller" refers to it being possible to draw the treatment portions 20, 54, 56, 60, 82, 130, 140, and 150 into the forceps channel of the endoscope without any hindrance. For example, in a case in which the main units 30, 84, 132, 142, and 152 are composed by an elastic material such as rubber and the outer peripheral portion thereof is rounded off, since the main unit 30, 84, 132, 142, or 152 can be drawn into the forceps channel without hindrance even when the outer dimensions of the main unit 30, 84, 132, 142, or 152 are approximately 10% larger than the inner dimensions of the forceps channel, the preferable size of the treatment portion 20, 54, 56, 60, 82, 130, 140, or 150 is approximately 110% or less with respect to the inner dimensions of the forceps channel.

The invention claimed is:

1. A treatment instrument for an endoscope comprising:
    an insertion portion having a distal end, a proximal end, and a longitudinal axis, to be inserted into a body, and
    a treatment portion disposed on the distal end of the insertion portion, wherein the treatment portion comprises:
        a proximal end portion connected to the insertion portion, a distal end portion on an opposite side of the proximal end portion, and a central axis extending in a direction of the longitudinal axis, and
        a plurality of plate-shaped members that pass through the central axis and are disposed in a radial shape around the central axis, and
    wherein one of said plurality of plate-shaped members comprises:
        a proximal end side peak portion protruding toward the insertion portion along the central axis, at a position distant from the central axis in the proximal end portion, and
        a distal end side peak portion protruding toward the opposite side of the insertion portion along the central axis, at a position distant from the central axis in the distal end portion,
        a cutting portion provided on at least one of
            a side of the proximal end portion closer to the central axis than the proximal end side peak portion, and
            a side of the distal end portion closer to the central axis than the distal end side peak portion, to cut a physical object in the body,
        wherein the distal end of the insertion portion directly connects to the proximal end portion of the treatment portion.

2. The treatment instrument for the endoscope according to claim 1, wherein the cutting portion is an electric conductor which is connected to a high-frequency current supply unit, a laser beam cutter, or an ultrasonic cutter.

3. The treatment instrument for the endoscope according to claim 1, further comprising the endoscope having a forceps channel,
    wherein the treatment portion is configured to be inserted through the forceps channel.

4. The treatment instrument for the endoscope according to claim 1, wherein in the treatment portion, a space between the proximal and distal end side peak portions is configured to expand and contract.

5. The treatment instrument for the endoscope according to claim 1, wherein the treatment portion is supported via a swivel mechanism which regulates a posture of the treatment portion.

6. The treatment instrument for the endoscope according to claim 1, further comprising:
    wherein the cutting portion comprises a plurality of cutting portions provided on said proximal or distal end portions; and
    a selection unit which selects one of the plurality of cutting portions to be used.

7. The treatment instrument for the endoscope according to claim 1, wherein the cutting portion is disposed at a position that is separate from an end face in a thickness direction of the treatment portion, the thickness direction being perpendicular to said central axis.

8. The treatment instrument for the endoscope according to claim 1, wherein at least one of the proximal end side peak portion and the distal end side peak portion is formed in a tapered shape which narrows towards a distal end side thereof, and a tip thereof is rounded and has a non-incisional property.

9. The treatment instrument according to claim 1, in which the insertion portion is thinner than the treatment portion.

10. The treatment instrument for the endoscope according to claim 1, wherein said plurality of plate-shaped members are non-conductive except for the cutting portion.

11. The treatment instrument for the endoscope according to claim 1, wherein the plurality of plate-shaped members have a longest dimension in a direction parallel to the longitudinal axis of the insertion portion.

12. A treatment instrument for an endoscope comprising:
    an insertion portion having a distal end, a proximal end, and a longitudinal axis, to be inserted into a body, and
    a treatment portion disposed on the distal end of the insertion portion, wherein the treatment portion comprises a proximal end portion connected to the insertion portion, a distal end portion on an opposite side of the proximal end portion, and a central axis collinear with the longitudinal axis,
    the treatment instrument further comprising:
    plate-shaped members that pass through the central axis and are disposed in a radial shape around the central axis, the plate shaped members having a longest dimension in a direction parallel to the longitudinal axis of the insertion portion;
    two or more peak portions protruding toward the distal end portion along the central axis, the two or more peak portions extending radially outwardly relative to the central axis and spaced from one another in a circumferential direction;
    a valley portion provided between two of the two or more peak portions; and
    a cutting portion provided on a bottom portion of the valley portion to cut a physical object in the body.

13. The treatment instrument according to claim 12, wherein the two or more peak portions are arranged in a circular distribution around the central axis.

14. The treatment instrument according to claim 13, in which the insertion portion is thinner than the treatment portion.

15. The treatment instrument according to claim 12, in which the insertion portion is thinner than the treatment portion.

16. A treatment instrument for an endoscope comprising:
    an insertion portion having a distal end, a proximal end, and a longitudinal axis, to be inserted into a body, and
    a treatment portion disposed on the distal end of the insertion portion, wherein the treatment portion comprises a proximal end portion connected to the insertion portion, a distal end portion on an opposite side of the proximal end portion, and a central axis extending in a direction of the longitudinal axis,
    the treatment instrument further comprising:
    three or more peak portions protruding toward the proximal end portion along the central axis;
    a valley portion provided between two of the three or more peak portions; and
    a first cutting portion provided on a bottom portion of the valley portion to cut a physical object in the body,
    wherein the distal end of the insertion portion directly connects to the proximal end portion of the treatment portion.

17. The treatment instrument according to claim 16, wherein the two or more peak portions are arranged in a circular distribution around the central axis.

18. The treatment instrument according to claim 17,
wherein the first cutting portion is at the distal end portion,
wherein the treatment portion further comprises a second cutting portion at the proximate end portion, and
whereby the second cutting portion can cut a physical object in the body.

19. The treatment instrument according to claim 18, in which the insertion portion is thinner than the treatment portion.

20. The treatment instrument according to claim 17, in which the insertion portion is thinner than the treatment portion.

21. The treatment instrument according to claim 16, in which the insertion portion is thinner than the treatment portion.

22. A treatment instrument for an endoscope, comprising
an insertion portion having a distal end, a proximal end and a longitudinal axis;
a wire extending through the insertion portion;
a treatment portion disposed on the distal end of the insertion portion, wherein the treatment portion comprises:
a main unit having a proximal end portion connected to the insertion portion and a distal end portion spaced from the proximal end portion, the main unit made of non-conductive material;
plate-shaped members extending radially outwardly from the main unit, the plate shaped members having a longest dimension in a direction parallel to the longitudinal axis of the insertion portion;
a conductor in the main unit, the conductor connected to the wire in the insertion portion; and
a first electrode plate embedded in a distal end of the main unit, the first electrode plate connected to the conductor,
wherein the main unit has at least two peak portions extending from the distal end of the main unit, the at least two peak portions forming a valley, and
wherein the first electrode plate is within the valley formed by the at least two peak portions.

23. The treatment instrument for the endoscope according to claim 22, further comprising:
a second electrode plate embedded in the proximal end of the main unit, the second electrode plate connected to the wire in the insertion portion and the conductor in the main unit.

* * * * *